(12) United States Patent
Day et al.

(10) Patent No.: US 8,658,591 B2
(45) Date of Patent: Feb. 25, 2014

(54) MULTI-LEU PEPTIDES AND ANALOGUES THEREOF AS SELECTIVE PACE4 INHIBITORS AND EFFECTIVE ANTIPROLIFERATIVE AGENTS

(76) Inventors: Robert Day, Sherbrooke (CA); Martin Fugère, San Diego, CA (US); Witold A. Neugebauer, Ottawa (CA)

( * ) Notice: Subject to any disclaimer, the term of this patent is extended or adjusted under 35 U.S.C. 154(b) by 0 days.

(21) Appl. No.: 13/003,628

(22) PCT Filed: Jul. 6, 2009

(86) PCT No.: PCT/CA2009/000935
§ 371 (c)(1),
(2), (4) Date: Mar. 9, 2011

(87) PCT Pub. No.: WO2010/003231
PCT Pub. Date: Jan. 14, 2010

(65) Prior Publication Data
US 2011/0178027 A1      Jul. 21, 2011

Related U.S. Application Data

(60) Provisional application No. 61/079,820, filed on Jul. 11, 2008.

(51) Int. Cl.
*A61K 38/00* (2006.01)
*A61P 35/00* (2006.01)

(52) U.S. Cl.
USPC .......... 514/1.1; 514/19.2; 514/19.3; 514/19.5

(58) Field of Classification Search
None
See application file for complete search history.

(56) References Cited

U.S. PATENT DOCUMENTS

| | | | |
|---|---|---|---|
| 5,604,201 A * | 2/1997 | Thomas et al. | 514/2.4 |
| 2003/0087827 A1 * | 5/2003 | Lindberg et al. | 514/14 |
| 2011/0236411 A1 * | 9/2011 | Scholler et al. | 424/193.1 |

FOREIGN PATENT DOCUMENTS

| WO | WO 2004/009113 A1 | 1/2004 |
|---|---|---|
| WO | WO 2005/025611 A1 | 3/2005 |
| WO | WO 2006/050611 * | 5/2006 |
| WO | WO 2008/137108 A2 | 11/2008 |

OTHER PUBLICATIONS

Tsuji A et al., Development of selectivity of alpha1-antitrypsin variant by mutagenesis in its reactive site loop against proprotein convertase. A crucial role of the P4 arginine in PACE4 inhibition. protein Engineering vol. 15 No. 2 pp. 123-130, 2002.*
Dasgupta et al, N-terminal acylation of somatostatin analog with long chain fatty acids enhances its stability and anti-proliferative activity in human breast adenocarcinoma cells, Biol Pharm Bull. Jan. 2002;25(1):29-36.*
Dasgupta et al, N-Terminal Acylation of Somatostatin Analog with Long Chain Fatty Acids Enhances Its Stability and Anti-Proliferative Activity in Human Breast Adenocarcinoma Cells, Biol. Pharm. Bull. 25(1) 29-36 (2002).*
Chicharro et al, N-Terminal Fatty Acid Substitution Increases the Leishmanicidal Activity of CA(1-7)M(2-9), a Cecropin-Melittin Hybrid Peptide, Antimicrobial Agents and Chemotherapy, Sep. 2001, p. 2441-2449.*
Dasgupta et al, Lipophilization of somatostatin analog RC-160 with long chain fatty acid improves its antiproliferative and antiangiogenic activity in vitro, British Journal of Pharmacology (2000) 129, 101-109.*
Basak, et al., "Recombinant proprotein convertase 4 (PC4) from Leishmania tarentolae expression system: Purification, biochemical study and inhibitor design"*Protein Expression and Purification*, 60, (2008) pp. 117-126.
Cameron, et al., "Polyarginines Are Potent Furin Inhibitors", *The Journal of Biological Chemistry*, vol. 275, No. 47, Issue of Nov. 24, pp. 36741-36749, 2000.
Tsuji, et al., "Development of selectivity of α1-antitrypsin variant by mutagenesis in its reactive site loop against proprotein convertase. A crucial role of the P4 arginine in PACE4 inhibition", *Protein Engineering*, vol. 15, No. 2, pp. 123-130, 2002.
Supplementary European Search Report for EP 09 79 3747, dated Jun. 13, 2012.
Tsuji, et al., A Proteomic Approach Reveals Transient Association of Reticulocalbin-3, a novel member of the CREC family, with the precursor of subtilisin-like proprotein convertase, PACE4. *Biochemical Journal*, vol. 396, No. 1, pp. 51-59, May 15, 2006.

* cited by examiner

*Primary Examiner* — Cecilia J Tsang
*Assistant Examiner* — Sergio Coffa
(74) *Attorney, Agent, or Firm* — Dority & Manning

(57) ABSTRACT

Disclosed herein are PACE4 inhibitors, compositions comprising PACE4 inhibitors and their uses thereof for lowering PACE4 activity, reducing cell proliferation, reducing tumor growth, reducing metastasis formation, preventing and/or treating cancer. Also provided are methods for lowering PACE4 activity, reducing the proliferation of a cell, reducing tumor growth and/or treating and preventing cancer. Methods for screening PACE4 inhibitors and cell proliferation inhibitors are further provided.

9 Claims, 12 Drawing Sheets

```
                         SEQUENCE LISTING

<160> NUMBER OF SEQ ID NOS: 107

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Val Lys Arg
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Arg Val Lys Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Leu Arg Val Lys Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Leu Arg Val Lys Arg
1               5

<210> SEQ ID NO 5
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Leu Leu Leu Leu Arg Val Lys Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Leu Leu Leu Leu Arg Val Lys Arg
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Leu Leu Leu Leu Leu Arg Val Lys Arg
1               5                   10

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagagaccc aggagcatcc c                                             21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acccgctggt ccgagtgct                                                19

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atccatcggg taccgggcca gctagtttgg cctctgctac caaccagggt ccacc        55

<210> SEQ ID NO 11
<211> LENGTH: 74
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 11
ccagctagaa agggtcccctt agccatccgc gaacggatgc ccaatcaaca ccgcgaggag    60
gtggaccctg gttg                                                      74

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaatacgac tcactataca aaaccaact ttggtacc                              38

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttaatacgac tcactatagg gccagctagt tt                                   32

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccagctagaa agggtcccctt a                                              21

<210> SEQ ID NO 15
<211> LENGTH: 260
<212> TYPE: PRT
<213> ORGANISM: Homo sapiens

<400> SEQUENCE: 15

Met Ala Gly Ser Pro Leu Leu Trp Gly Pro Arg Ala Gly Gly Val Gly
1               5                   10                  15

Leu Leu Val Leu Leu Leu Leu Gly Leu Phe Arg Pro Pro Ala Leu
            20                  25                  30

Cys Ala Arg Pro Val Lys Glu Pro Arg Gly Leu Ser Ala Ala Ser Pro
        35                  40                  45

Pro Leu Ala Glu Thr Gly Ala Pro Arg Arg Phe Arg Arg Ser Val Pro
    50                  55                  60

Arg Gly Glu Ala Ala Gly Ala Val Gln Glu Leu Ala Arg Ala Leu Ala
65                  70                  75                  80

His Leu Leu Glu Ala Glu Arg Gln Glu Arg Ala Arg Ala Glu Ala Gln
                85                  90                  95

Glu Ala Glu Asp Gln Gln Ala Arg Val Leu Ala Gln Leu Leu Arg Val
                100                 105                 110

Trp Gly Ala Pro Arg Asn Ser Asp Pro Ala Leu Gly Leu Asp Asp Asp

```
            115                 120                 125
Pro Asp Ala Pro Ala Gln Leu Ala Arg Ala Leu Leu Arg Ala Arg
    130                 135                 140
Leu Asp Pro Ala Ala Leu Ala Ala Gln Leu Val Pro Ala Pro Val Pro
145                 150                 155                 160
Ala Ala Ala Leu Arg Pro Arg Pro Val Tyr Asp Asp Gly Pro Ala
                165                 170                 175
Gly Pro Asp Ala Glu Glu Ala Gly Asp Glu Thr Pro Asp Val Asp Pro
                    180                 185                 190
Glu Leu Leu Arg Tyr Leu Leu Gly Arg Ile Leu Ala Gly Ser Ala Asp
                195                 200                 205
Ser Glu Gly Val Ala Ala Pro Arg Arg Leu Arg Ala Ala Asp His
    210                 215                 220
Asp Val Gly Ser Glu Leu Pro Pro Glu Gly Val Leu Gly Ala Leu Leu
225                 230                 235                 240
Arg Val Lys Arg Leu Glu Thr Pro Ala Pro Gln Val Pro Ala Arg Arg
                    245                 250                 255
Leu Leu Pro Pro
        260

<210> SEQ ID NO 16
<211> LENGTH: 31
<212> TYPE: PRT
<213> ORGANISM: Homo sapiens

<400> SEQUENCE: 16

Ser Val Asn Pro Tyr Leu Gln Gly Gln Arg Leu Asp Asn Val Val Ala
1               5                   10                  15
Lys Lys Ser Val Pro His Phe Ser Asp Glu Lys Asp Pro Glu
            20                  25                  30

<210> SEQ ID NO 17
<211> LENGTH: 913
<212> TYPE: PRT
<213> ORGANISM: Homo sapiens

<400> SEQUENCE: 17

Met Gly Trp Gly Ser Arg Cys Cys Pro Gly Arg Leu Asp Leu Leu
1               5                   10                  15
Cys Val Leu Ala Leu Leu Gly Gly Cys Leu Leu Pro Val Cys Arg Thr
                20                  25                  30
Arg Val Tyr Thr Asn His Trp Ala Val Lys Ile Ala Gly Gly Phe Pro
            35                  40                  45
Glu Ala Asn Arg Ile Ala Ser Lys Tyr Gly Phe Ile Asn Ile Gly Gln
        50                  55                  60
Ile Gly Ala Leu Lys Asp Tyr Tyr His Phe Tyr His Ser Arg Thr Ile
65                  70                  75                  80
Lys Arg Ser Val Ile Ser Ser Arg Gly Thr His Ser Phe Ile Ser Met
                85                  90                  95
Glu Pro Lys Val Glu Trp Ile Gln Gln Gln Val Val Lys Lys Arg Thr
                100                 105                 110
Lys Arg Asp Tyr Asp Phe Ser Arg Ala Gln Ser Thr Tyr Phe Asn Asp
            115                 120                 125
Pro Lys Trp Pro Ser Met Trp Tyr Met His Cys Ser Asp Asn Thr His
        130                 135                 140
Pro Cys Gln Ser Asp Met Asn Ile Glu Gly Ala Trp Lys Arg Gly Tyr
145                 150                 155                 160
```

```
Thr Gly Lys Asn Ile Val Val Thr Ile Leu Asp Asp Gly Ile Glu Arg
                165                 170                 175
Thr His Pro Asp Leu Met Gln Asn Tyr Asp Ala Leu Ala Ser Cys Asp
            180                 185                 190
Val Asn Gly Asn Asp Leu Asp Pro Met Pro Arg Tyr Asp Ala Ser Asn
        195                 200                 205
Glu Asn Lys His Gly Thr Arg Cys Ala Gly Glu Val Ala Ala Ala Ala
    210                 215                 220
Asn Asn Ser His Cys Thr Val Gly Ile Ala Phe Asn Ala Lys Ile Gly
225                 230                 235                 240
Gly Val Arg Met Leu Asp Gly Asp Val Thr Asp Met Val Glu Ala Lys
                245                 250                 255
Ser Val Ser Phe Asn Pro Gln His Val His Ile Tyr Ser Ala Ser Trp
            260                 265                 270
Gly Pro Asp Asp Asp Gly Lys Thr Val Asp Gly Pro Ala Pro Leu Thr
        275                 280                 285
Arg Gln Ala Phe Glu Asn Gly Val Arg Met Gly Arg Arg Gly Leu Gly
    290                 295                 300
Ser Val Phe Val Trp Ala Ser Gly Asn Gly Gly Arg Ser Lys Asp His
305                 310                 315                 320
Cys Ser Cys Asp Gly Tyr Thr Asn Ser Ile Tyr Thr Ile Ser Ile Ser
                325                 330                 335
Ser Thr Ala Glu Ser Gly Lys Lys Pro Trp Tyr Leu Glu Glu Cys Ser
            340                 345                 350
Ser Thr Leu Ala Thr Thr Tyr Ser Ser Gly Glu Ser Tyr Asp Lys Lys
        355                 360                 365
Ile Ile Thr Thr Asp Leu Arg Gln Arg Cys Thr Asp Asn His Thr Gly
    370                 375                 380
Thr Ser Ala Ser Ala Pro Met Ala Ala Gly Ile Ile Ala Leu Ala Leu
385                 390                 395                 400
Glu Ala Asn Pro Phe Leu Thr Trp Arg Asp Val Gln His Val Ile Val
                405                 410                 415
Arg Thr Ser Arg Ala Gly His Leu Asn Ala Asn Asp Trp Lys Thr Asn
            420                 425                 430
Ala Ala Gly Phe Lys Val Ser His Leu Tyr Gly Phe Gly Leu Met Asp
        435                 440                 445
Ala Glu Ala Met Val Met Glu Ala Glu Lys Trp Thr Thr Val Pro Arg
    450                 455                 460
Gln His Val Cys Val Glu Ser Thr Asp Arg Gln Ile Lys Thr Ile Arg
465                 470                 475                 480
Pro Asn Ser Ala Val Arg Ser Ile Tyr Lys Ala Ser Gly Cys Ser Asp
                485                 490                 495
Asn Pro Asn Arg His Val Asn Tyr Leu Glu His Val Val Val Arg Ile
            500                 505                 510
Thr Ile Thr His Pro Arg Arg Gly Asp Leu Ala Ile Tyr Leu Thr Ser
        515                 520                 525
Pro Ser Gly Thr Arg Ser Gln Leu Leu Ala Asn Arg Leu Phe Asp His
    530                 535                 540
Ser Met Glu Gly Phe Lys Asn Trp Glu Phe Met Thr Ile His Cys Trp
545                 550                 555                 560
Gly Glu Arg Ala Ala Gly Asp Trp Val Leu Glu Val Tyr Asp Thr Pro
                565                 570                 575
Ser Gln Leu Arg Asn Phe Lys Thr Pro Gly Lys Leu Lys Glu Trp Ser
```

```
                      580                 585                 590
Leu Val Leu Tyr Gly Thr Ser Val Gln Pro Tyr Ser Pro Thr Asn Glu
            595                 600                 605

Phe Pro Lys Val Glu Arg Phe Arg Tyr Ser Arg Val Glu Asp Pro Thr
            610                 615                 620

Asp Asp Tyr Gly Thr Glu Asp Tyr Ala Gly Pro Cys Asp Pro Glu Cys
625                 630                 635                 640

Ser Glu Val Gly Cys Asp Gly Pro Gly Asp His Cys Asn Asp Cys
                645                 650                 655

Leu His Tyr Tyr Tyr Lys Leu Lys Asn Asn Thr Arg Ile Cys Val Ser
            660                 665                 670

Ser Cys Pro Pro Gly His Tyr His Ala Asp Lys Lys Arg Cys Arg Lys
            675                 680                 685

Cys Ala Pro Asn Cys Glu Ser Cys Phe Gly Ser His Gly Asp Gln Cys
            690                 695                 700

Met Ser Cys Lys Tyr Gly Tyr Phe Leu Asn Glu Glu Thr Asn Ser Cys
705                 710                 715                 720

Val Thr His Cys Pro Asp Gly Ser Tyr Gln Asp Thr Lys Lys Asn Leu
                725                 730                 735

Cys Arg Lys Cys Ser Glu Asn Cys Lys Thr Cys Thr Glu Phe His Asn
            740                 745                 750

Cys Thr Glu Cys Arg Asp Gly Leu Ser Leu Gln Gly Ser Arg Cys Ser
            755                 760                 765

Val Ser Cys Glu Asp Gly Arg Tyr Phe Asn Gly Gln Asp Cys Gln Pro
770                 775                 780

Cys His Arg Phe Cys Ala Thr Cys Ala Gly Ala Gly Ala Asp Gly Cys
785                 790                 795                 800

Ile Asn Cys Thr Glu Gly Tyr Phe Met Glu Asp Gly Arg Cys Val Gln
                805                 810                 815

Ser Cys Ser Ile Ser Tyr Tyr Phe Asp His Ser Ser Glu Asn Gly Tyr
            820                 825                 830

Lys Ser Cys Lys Lys Cys Asp Ile Ser Cys Leu Thr Cys Asn Gly Pro
            835                 840                 845

Gly Phe Lys Asn Cys Thr Ser Cys Pro Ser Gly Tyr Leu Leu Asp Leu
850                 855                 860

Gly Met Cys Gln Met Gly Ala Ile Cys Lys Asp Ala Thr Glu Glu Ser
865                 870                 875                 880

Trp Ala Glu Gly Gly Phe Cys Met Leu Val Lys Lys Asn Asn Leu Cys
                885                 890                 895

Gln Arg Lys Val Leu Gln Gln Leu Cys Cys Lys Thr Cys Thr Phe Gln
            900                 905                 910

Gly

<210> SEQ ID NO 18
<211> LENGTH: 784
<212> TYPE: PRT
<213> ORGANISM: Homo sapiens

<400> SEQUENCE: 18

Met Pro Lys Gly Arg Gln Lys Val Pro His Leu Asp Ala Pro Leu Gly
1               5                   10                  15

Leu Pro Thr Cys Leu Trp Leu Glu Leu Ala Gly Leu Phe Leu Leu Val
                20                  25                  30

Pro Trp Val Met Gly Leu Ala Gly Thr Gly Gly Pro Asp Gly Gln Gly
            35                  40                  45
```

```
Thr Gly Gly Pro Ser Trp Ala Val His Leu Glu Ser Leu Glu Gly Asp
 50                  55                  60

Gly Glu Glu Glu Thr Leu Glu Gln Gln Ala Asp Ala Leu Ala Gln Ala
 65                  70                  75                  80

Ala Gly Leu Val Asn Ala Gly Arg Ile Gly Glu Leu Gln Gly His Tyr
                 85                  90                  95

Leu Phe Val Gln Pro Ala Gly His Arg Pro Ala Leu Glu Val Glu Ala
             100                 105                 110

Ile Arg Gln Gln Val Glu Ala Val Leu Ala Gly His Glu Ala Val Arg
         115                 120                 125

Trp His Ser Glu Gln Arg Leu Leu Arg Arg Ala Lys Arg Ser Val His
 130                 135                 140

Phe Asn Asp Pro Lys Tyr Pro Gln Gln Trp His Leu Asn Asn Arg Arg
145                 150                 155                 160

Ser Pro Gly Arg Asp Ile Asn Val Thr Gly Val Trp Glu Arg Asn Val
                165                 170                 175

Thr Gly Arg Gly Val Thr Val Val Val Asp Asp Gly Val Glu His
            180                 185                 190

Thr Ile Gln Asp Ile Ala Pro Asn Tyr Ser Pro Glu Gly Ser Tyr Asp
        195                 200                 205

Leu Asn Ser Asn Asp Pro Asp Pro Met Pro His Pro Asp Val Glu Asn
210                 215                 220

Gly Asn His His Gly Thr Arg Cys Ala Gly Glu Ile Ala Ala Val Pro
225                 230                 235                 240

Asn Asn Ser Phe Cys Ala Val Gly Val Ala Tyr Gly Ser Arg Ile Ala
                245                 250                 255

Gly Ile Arg Val Leu Asp Gly Pro Leu Thr Asp Ser Met Glu Ala Val
            260                 265                 270

Ala Phe Asn Lys His Tyr Gln Ile Asn Asp Ile Tyr Ser Cys Ser Trp
        275                 280                 285

Gly Pro Asp Asp Asp Gly Lys Thr Val Asp Gly Pro His Gln Leu Gly
290                 295                 300

Lys Ala Ala Leu Gln His Gly Val Ile Ala Gly Arg Gln Gly Phe Gly
305                 310                 315                 320

Ser Ile Phe Val Val Ala Ser Gly Asn Gly Gln His Asn Asp Asn
                325                 330                 335

Cys Asn Tyr Asp Gly Tyr Ala Asn Ser Ile Tyr Thr Val Thr Ile Gly
            340                 345                 350

Ala Val Asp Glu Glu Gly Arg Met Pro Phe Tyr Ala Glu Glu Cys Ala
        355                 360                 365

Ser Met Leu Ala Val Thr Phe Ser Gly Gly Asp Lys Met Leu Arg Ser
370                 375                 380

Ile Val Thr Thr Asp Trp Asp Leu Gln Lys Gly Thr Gly Cys Thr Glu
385                 390                 395                 400

Gly His Thr Gly Thr Ser Ala Ala Pro Leu Ala Ala Gly Met Ile
                405                 410                 415

Ala Leu Met Leu Gln Val Arg Pro Cys Leu Thr Trp Arg Asp Val Gln
            420                 425                 430

His Ile Ile Val Phe Thr Ala Thr Arg Tyr Glu Asp Arg Arg Ala Glu
        435                 440                 445

Trp Val Thr Asn Glu Ala Gly Phe Ser His Ser His Gln His Gly Phe
450                 455                 460

Gly Leu Leu Asn Ala Trp Arg Leu Val Asn Ala Ala Lys Ile Trp Thr
```

```
                465                 470                 475                 480
Ser Val Pro Tyr Leu Ala Ser Tyr Val Ser Pro Val Leu Lys Glu Asn
                    485                 490                 495

Lys Ala Ile Pro Gln Ser Pro Arg Ser Leu Glu Val Leu Trp Asn Val
                500                 505                 510

Ser Arg Met Asp Leu Glu Met Gly Leu Lys Thr Leu Glu His Val Ala
            515                 520                 525

Val Thr Val Ser Ile Thr His Pro Arg Arg Gly Ser Leu Glu Leu Lys
        530                 535                 540

Leu Phe Cys Pro Ser Gly Met Met Ser Leu Ile Gly Ala Pro Arg Ser
545                 550                 555                 560

Met Asp Ser Asp Pro Asn Gly Phe Asn Asp Trp Thr Phe Ser Thr Val
                565                 570                 575

Arg Cys Trp Gly Glu Arg Ala Arg Gly Thr Tyr Arg Leu Val Ile Arg
                580                 585                 590

Asp Val Gly Asp Glu Ser Phe Gln Val Gly Ile Leu Arg Gln Trp Gln
            595                 600                 605

Leu Thr Leu Tyr Gly Ser Val Trp Ser Ala Val Asp Ile Arg Asp Arg
        610                 615                 620

Gln Arg Leu Leu Glu Ser Ala Met Ser Gly Lys Tyr Leu His Asp Asp
625                 630                 635                 640

Phe Ala Leu Pro Cys Pro Pro Gly Leu Lys Ile Pro Glu Glu Asp Gly
                645                 650                 655

Tyr Thr Ile Thr Pro Asn Thr Leu Lys Thr Leu Val Leu Val Gly Cys
                660                 665                 670

Phe Thr Val Phe Trp Thr Val Tyr Tyr Met Leu Glu Val Tyr Leu Ser
            675                 680                 685

Gln Arg Asn Val Ala Ser Asn Gln Val Cys Arg Ser Gly Pro Cys His
        690                 695                 700

Trp Pro His Arg Ser Arg Lys Ala Lys Glu Glu Gly Thr Glu Leu Glu
705                 710                 715                 720

Ser Val Pro Leu Cys Ser Ser Lys Asp Pro Asp Glu Val Glu Thr Glu
                725                 730                 735

Ser Arg Gly Pro Pro Thr Thr Ser Asp Leu Leu Ala Pro Asp Leu Leu
                740                 745                 750

Glu Gln Gly Asp Trp Ser Leu Ser Gln Asn Lys Ser Ala Leu Asp Cys
            755                 760                 765

Pro His Gln His Leu Asp Val Pro His Gly Lys Glu Glu Gln Ile Cys
        770                 775                 780

<210> SEQ ID NO 19
<211> LENGTH: 794
<212> TYPE: PRT
<213> ORGANISM: Homo sapiens

<400> SEQUENCE: 19

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
```

-continued

```
               65                  70                  75                  80
        Arg Pro Arg His Ser Arg Leu Gln Arg Glu Pro Gln Val Gln Trp Leu
                            85                  90                  95
        Glu Gln Gln Val Ala Lys Arg Thr Lys Arg Asp Val Tyr Gln Glu
                       100                 105                 110
        Pro Thr Asp Pro Lys Phe Pro Gln Gln Trp Tyr Leu Ser Gly Val Thr
                       115                 120                 125
        Gln Arg Asp Leu Asn Val Lys Ala Ala Trp Ala Gln Gly Tyr Thr Gly
                       130                 135                 140
        His Gly Ile Val Ser Ile Leu Asp Asp Gly Ile Glu Lys Asn His
        145                 150                 155                 160
        Pro Asp Leu Ala Gly Asn Tyr Asp Pro Gly Ala Ser Phe Asp Val Asn
                       165                 170                 175
        Asp Gln Asp Pro Asp Pro Gln Pro Arg Tyr Thr Gln Met Asn Asp Asn
                       180                 185                 190
        Arg His Gly Thr Arg Cys Ala Gly Glu Val Ala Ala Val Ala Asn Asn
                       195                 200                 205
        Gly Val Cys Gly Val Gly Val Ala Tyr Asn Ala Arg Ile Gly Gly Val
                       210                 215                 220
        Arg Met Leu Asp Gly Glu Val Thr Asp Ala Val Glu Ala Arg Ser Leu
        225                 230                 235                 240
        Gly Leu Asn Pro Asn His Ile His Ile Tyr Ser Ala Ser Trp Gly Pro
                       245                 250                 255
        Glu Asp Asp Gly Lys Thr Val Asp Gly Pro Ala Arg Leu Ala Glu Glu
                       260                 265                 270
        Ala Phe Phe Arg Gly Val Ser Gln Gly Arg Gly Gly Leu Gly Ser Ile
                       275                 280                 285
        Phe Val Trp Ala Ser Gly Asn Gly Gly Arg Glu His Asp Ser Cys Asn
                       290                 295                 300
        Cys Asp Gly Tyr Thr Asn Ser Ile Tyr Thr Leu Ser Ile Ser Ser Ala
        305                 310                 315                 320
        Thr Gln Phe Gly Asn Val Pro Trp Tyr Ser Glu Ala Cys Ser Ser Thr
                       325                 330                 335
        Leu Ala Thr Thr Tyr Ser Ser Gly Asn Gln Asn Glu Lys Gln Ile Val
                       340                 345                 350
        Thr Thr Asp Leu Arg Gln Lys Cys Thr Glu Ser His Thr Gly Thr Ser
                       355                 360                 365
        Ala Ser Ala Pro Leu Ala Ala Gly Ile Ile Ala Leu Thr Leu Glu Ala
                       370                 375                 380
        Asn Lys Asn Leu Thr Trp Arg Asp Met Gln His Leu Val Val Gln Thr
        385                 390                 395                 400
        Ser Lys Pro Ala His Leu Asn Ala Asn Asp Trp Ala Thr Asn Gly Val
                       405                 410                 415
        Gly Arg Lys Val Ser His Ser Tyr Gly Tyr Gly Leu Leu Asp Ala Gly
                       420                 425                 430
        Ala Met Val Ala Leu Ala Gln Asn Trp Thr Thr Val Ala Pro Gln Arg
                       435                 440                 445
        Lys Cys Ile Ile Asp Ile Leu Thr Glu Pro Lys Asp Ile Gly Lys Arg
                       450                 455                 460
        Leu Glu Val Arg Lys Thr Val Thr Ala Cys Leu Gly Glu Pro Asn His
        465                 470                 475                 480
        Ile Thr Arg Leu Glu His Ala Gln Ala Arg Leu Thr Leu Ser Tyr Asn
                       485                 490                 495
```

-continued

```
Arg Arg Gly Asp Leu Ala Ile His Leu Val Ser Pro Met Gly Thr Arg
        500                 505                 510
Ser Thr Leu Leu Ala Ala Arg Pro His Asp Tyr Ser Ala Asp Gly Phe
        515                 520                 525
Asn Asp Trp Ala Phe Met Thr Thr His Ser Trp Asp Glu Asp Pro Ser
        530                 535                 540
Gly Glu Trp Val Leu Glu Ile Glu Asn Thr Ser Glu Ala Asn Asn Tyr
545                 550                 555                 560
Gly Thr Leu Thr Lys Phe Thr Leu Val Leu Tyr Gly Thr Ala Pro Glu
                565                 570                 575
Gly Leu Pro Val Pro Pro Glu Ser Ser Gly Cys Lys Thr Leu Thr Ser
                580                 585                 590
Ser Gln Ala Cys Val Val Cys Glu Glu Gly Phe Ser Leu His Gln Lys
                595                 600                 605
Ser Cys Val Gln His Cys Pro Pro Gly Phe Ala Pro Gln Val Leu Asp
        610                 615                 620
Thr His Tyr Ser Thr Glu Asn Asp Val Glu Thr Ile Arg Ala Ser Val
625                 630                 635                 640
Cys Ala Pro Cys His Ala Ser Cys Ala Thr Cys Gln Gly Pro Ala Leu
                645                 650                 655
Thr Asp Cys Leu Ser Cys Pro Ser His Ala Ser Leu Asp Pro Val Glu
                660                 665                 670
Gln Thr Cys Ser Arg Gln Ser Gln Ser Ser Arg Glu Ser Pro Pro Gln
                675                 680                 685
Gln Gln Pro Pro Arg Leu Pro Pro Glu Val Glu Ala Gly Gln Arg Leu
        690                 695                 700
Arg Ala Gly Leu Leu Pro Ser His Leu Pro Glu Val Val Ala Gly Leu
705                 710                 715                 720
Ser Cys Ala Phe Ile Val Leu Val Phe Val Thr Val Phe Leu Val Leu
                725                 730                 735
Gln Leu Arg Ser Gly Phe Ser Phe Arg Gly Val Lys Val Tyr Thr Met
                740                 745                 750
Asp Arg Gly Leu Ile Ser Tyr Lys Gly Leu Pro Pro Glu Ala Trp Gln
                755                 760                 765
Glu Glu Cys Pro Ser Asp Ser Glu Glu Asp Glu Gly Arg Gly Glu Arg
        770                 775                 780
Thr Ala Phe Ile Lys Asp Gln Ser Ala Leu
785                 790

<210> SEQ ID NO 20
<211> LENGTH: 638
<212> TYPE: PRT
<213> ORGANISM: Homo sapiens

<400> SEQUENCE: 20

Met Lys Gly Gly Cys Val Ser Gln Trp Lys Ala Ala Gly Phe Leu
1               5                   10                  15
Phe Cys Val Met Val Phe Ala Ser Ala Glu Arg Pro Val Phe Thr Asn
                20                  25                  30
His Phe Leu Val Glu Leu His Lys Gly Gly Glu Asp Lys Ala Arg Gln
        35                  40                  45
Val Ala Ala Glu His Gly Phe Gly Val Arg Lys Leu Pro Phe Ala Glu
        50                  55                  60
Gly Leu Tyr His Phe Tyr His Asn Gly Leu Ala Lys Ala Lys Arg Arg
65                  70                  75                  80
```

```
Arg Ser Leu His His Lys Gln Gln Leu Glu Arg Asp Pro Arg Val Lys
             85                  90                  95

Met Ala Leu Gln Gln Glu Gly Phe Asp Arg Lys Arg Gly Tyr Arg
            100                 105                 110

Asp Ile Asn Glu Ile Asp Ile Asn Met Asn Asp Pro Leu Phe Thr Lys
            115                 120                 125

Gln Trp Tyr Leu Ile Asn Thr Gly Gln Ala Asp Gly Thr Pro Gly Leu
        130                 135                 140

Asp Leu Asn Val Ala Glu Ala Trp Glu Leu Gly Tyr Thr Gly Lys Gly
145                 150                 155                 160

Val Thr Ile Gly Ile Met Asp Asp Gly Ile Asp Tyr Leu His Pro Asp
                165                 170                 175

Leu Ala Ser Asn Tyr Asn Ala Glu Ala Ser Tyr Asp Phe Ser Ser Asn
            180                 185                 190

Asp Pro Tyr Pro Tyr Pro Arg Tyr Thr Asp Asp Trp Phe Asn Ser His
            195                 200                 205

Gly Thr Arg Cys Ala Gly Glu Val Ser Ala Ala Asn Asn Asn Ile
        210                 215                 220

Cys Gly Val Gly Val Ala Tyr Asn Ser Lys Val Ala Gly Ile Arg Met
225                 230                 235                 240

Leu Asp Gln Pro Phe Met Thr Asp Ile Ile Glu Ala Ser Ser Ile Ser
                245                 250                 255

His Met Pro Gln Leu Ile Asp Ile Tyr Ser Ala Ser Trp Gly Pro Thr
            260                 265                 270

Asp Asn Gly Lys Thr Val Asp Gly Pro Arg Glu Leu Thr Leu Gln Ala
            275                 280                 285

Met Ala Asp Gly Val Asn Lys Gly Arg Gly Lys Gly Ser Ile Tyr
        290                 295                 300

Val Trp Ala Ser Gly Asp Gly Gly Ser Tyr Asp Cys Asn Cys Asp
305                 310                 315                 320

Gly Tyr Ala Ser Ser Met Trp Thr Ile Ser Ile Asn Ser Ala Ile Asn
                325                 330                 335

Asp Gly Arg Thr Ala Leu Tyr Asp Glu Ser Cys Ser Ser Thr Leu Ala
            340                 345                 350

Ser Thr Phe Ser Asn Gly Arg Lys Arg Asn Pro Glu Ala Gly Val Ala
        355                 360                 365

Thr Thr Asp Leu Tyr Gly Asn Cys Thr Leu Arg His Ser Gly Thr Ser
        370                 375                 380

Ala Ala Ala Pro Glu Ala Gly Val Phe Ala Leu Ala Leu Glu Ala
385                 390                 395                 400

Asn Leu Gly Leu Thr Trp Arg Asp Met Gln His Leu Thr Val Leu Thr
                405                 410                 415

Ser Lys Arg Asn Gln Leu His Asp Glu Val His Gln Trp Arg Arg Asn
            420                 425                 430

Gly Val Gly Leu Glu Phe Asn His Leu Phe Gly Tyr Gly Val Leu Asp
        435                 440                 445

Ala Gly Ala Met Val Lys Met Ala Lys Asp Trp Lys Thr Val Pro Glu
        450                 455                 460

Arg Phe His Cys Val Gly Gly Ser Val Gln Asp Pro Glu Lys Ile Pro
465                 470                 475                 480

Ser Thr Gly Lys Leu Val Leu Thr Leu Thr Thr Asp Ala Cys Glu Gly
                485                 490                 495

Lys Glu Asn Phe Val Arg Tyr Leu Glu His Val Gln Ala Val Ile Thr
            500                 505                 510
```

Val Asn Ala Thr Arg Arg Gly Asp Leu Asn Ile Asn Met Thr Ser Pro
            515                 520                 525

Met Gly Thr Lys Ser Ile Leu Leu Ser Arg Arg Pro Arg Asp Asp Asp
        530                 535                 540

Ser Lys Val Gly Phe Asp Lys Trp Pro Phe Met Thr Thr His Thr Trp
545                 550                 555                 560

Gly Glu Asp Ala Arg Gly Thr Trp Thr Leu Glu Leu Gly Phe Val Gly
                565                 570                 575

Ser Ala Pro Gln Lys Gly Val Leu Lys Glu Trp Thr Leu Met Leu His
            580                 585                 590

Gly Thr Gln Ser Ala Pro Tyr Ile Asp Gln Val Val Arg Asp Tyr Gln
        595                 600                 605

Ser Lys Leu Ala Met Ser Lys Lys Glu Glu Leu Glu Glu Leu Asp
    610                 615                 620

Glu Ala Val Glu Arg Ser Leu Lys Ser Ile Leu Asn Lys Asn
625                 630                 635

<210> SEQ ID NO 21
<211> LENGTH: 753
<212> TYPE: PRT
<213> ORGANISM: Homo sapiens

<400> SEQUENCE: 21

Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

```
Asn Pro Gly His Val Asp Ile Tyr Ser Ala Ser Trp Gly Pro Asn Asp
            260                 265                 270

Asp Gly Lys Thr Val Glu Gly Pro Arg Leu Ala Gln Lys Ala Phe
        275                 280                 285

Glu Tyr Gly Val Lys Gln Gly Arg Gln Gly Lys Gly Ser Ile Phe Val
        290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
                340                 345                 350

Thr Ser Tyr Ser Ser Gly Asp Tyr Thr Asp Gln Arg Ile Thr Ser Ala
                355                 360                 365

Asp Leu His Asn Asp Cys Thr Glu Thr His Thr Gly Thr Ser Ala Ser
        370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
                420                 425                 430

Leu Met Val Asn Ser Arg Phe Gly Phe Gly Leu Leu Asn Ala Lys Ala
                435                 440                 445

Leu Val Asp Leu Ala Asp Pro Arg Thr Trp Arg Ser Val Pro Glu Lys
        450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
        500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
        530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
                580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
        610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
                645                 650                 655

Glu Leu Glu Glu Gly Ala Pro Ser Gln Ala Met Leu Arg Leu Leu Gln
        660                 665                 670

Ser Ala Phe Ser Lys Asn Ser Pro Pro Lys Gln Ser Pro Lys Lys Ser
```

```
                    675                 680                 685
Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn

<210> SEQ ID NO 22
<211> LENGTH: 755
<212> TYPE: PRT
<213> ORGANISM: Homo sapiens

<400> SEQUENCE: 22

Met Arg Pro Ala Pro Ile Ala Leu Trp Leu Arg Leu Val Leu Ala Leu
1               5                   10                  15

Ala Leu Val Arg Pro Arg Ala Val Gly Trp Ala Pro Arg Ala Pro
            20                  25                  30

Ile Tyr Val Ser Ser Trp Ala Val Gln Val Ser Gln Gly Asn Arg Glu
            35                  40                  45

Val Glu Arg Leu Ala Arg Lys Phe Gly Phe Val Asn Leu Gly Pro Ile
50                  55                  60

Phe Pro Asp Gly Gln Tyr Phe His Leu Arg His Arg Gly Val Val Gln
65                  70                  75                  80

Gln Ser Leu Thr Pro His Trp Gly His Arg Leu His Leu Lys Lys Asn
                85                  90                  95

Pro Lys Val Gln Trp Phe Gln Gln Thr Leu Gln Arg Arg Val Lys
            100                 105                 110

Arg Ser Val Val Val Pro Thr Asp Pro Trp Phe Ser Lys Gln Trp Tyr
            115                 120                 125

Met Asn Ser Glu Ala Gln Pro Asp Leu Ser Ile Leu Gln Ala Trp Ser
    130                 135                 140

Gln Gly Leu Ser Gly Gln Gly Ile Val Val Ser Val Leu Asp Asp Gly
145                 150                 155                 160

Ile Glu Lys Asp His Pro Asp Leu Trp Ala Asn Tyr Asp Pro Leu Ala
                165                 170                 175

Ser Tyr Asp Phe Asn Asp Tyr Asp Pro Asp Pro Gln Pro Arg Tyr Thr
            180                 185                 190

Pro Ser Lys Glu Asn Arg His Gly Thr Arg Cys Ala Gly Glu Val Ala
            195                 200                 205

Ala Met Ala Asn Asn Gly Phe Cys Gly Val Gly Val Ala Phe Asn Ala
    210                 215                 220

Arg Ile Gly Gly Val Arg Met Leu Asp Gly Thr Ile Thr Asp Val Ile
225                 230                 235                 240

Glu Ala Gln Ser Leu Ser Leu Gln Pro Gln His Ile His Ile Tyr Ser
                245                 250                 255

Ala Ser Trp Gly Pro Glu Asp Asp Gly Arg Thr Val Asp Gly Pro Gly
            260                 265                 270

Ile Leu Thr Arg Glu Ala Phe Arg Arg Gly Val Thr Lys Gly Arg Gly
            275                 280                 285

Gly Leu Gly Thr Leu Phe Ile Trp Ala Ser Gly Asn Gly Gly Leu His
    290                 295                 300
```

```
Tyr Asp Asn Cys Asn Cys Asp Gly Tyr Thr Asn Ser Ile His Thr Leu
305                 310                 315                 320

Ser Val Gly Ser Thr Thr Gln Gln Gly Arg Val Pro Trp Tyr Ser Glu
            325                 330                 335

Ala Cys Ala Ser Thr Leu Thr Thr Thr Tyr Ser Ser Gly Val Ala Thr
            340                 345                 350

Asp Pro Gln Ile Val Thr Thr Asp Leu His His Gly Cys Thr Asp Gln
            355                 360                 365

His Thr Gly Thr Ser Ala Ser Ala Pro Leu Ala Ala Gly Met Ile Ala
        370                 375                 380

Leu Ala Leu Glu Ala Asn Pro Phe Leu Thr Trp Arg Asp Met Gln His
385                 390                 395                 400

Leu Val Val Arg Ala Ser Lys Pro Ala His Leu Gln Ala Glu Asp Trp
                405                 410                 415

Arg Thr Asn Gly Val Gly Arg Gln Val Ser His His Tyr Gly Tyr Gly
            420                 425                 430

Leu Leu Asp Ala Gly Leu Leu Val Asp Thr Ala Arg Thr Trp Leu Pro
        435                 440                 445

Thr Gln Pro Gln Arg Lys Cys Ala Val Arg Val Gln Ser Arg Pro Thr
    450                 455                 460

Pro Ile Leu Pro Leu Ile Tyr Ile Arg Glu Asn Val Ser Ala Cys Ala
465                 470                 475                 480

Gly Leu His Asn Ser Ile Arg Ser Leu Glu His Val Gln Ala Gln Leu
                485                 490                 495

Thr Leu Ser Tyr Ser Arg Arg Gly Asp Leu Glu Ile Ser Leu Thr Ser
            500                 505                 510

Pro Met Gly Thr Arg Ser Thr Leu Val Ala Ile Arg Pro Leu Asp Val
            515                 520                 525

Ser Thr Glu Gly Tyr Asn Asn Trp Val Phe Met Ser Thr His Phe Trp
    530                 535                 540

Asp Glu Asn Pro Gln Gly Val Trp Thr Leu Gly Leu Glu Asn Lys Gly
545                 550                 555                 560

Tyr Tyr Phe Asn Thr Gly Thr Leu Tyr Arg Tyr Thr Leu Leu Leu Tyr
                565                 570                 575

Gly Thr Ala Glu Asp Met Thr Ala Arg Pro Thr Gly Pro Gln Val Thr
            580                 585                 590

Ser Ser Ala Cys Val Gln Arg Asp Thr Glu Gly Leu Cys Gln Ala Cys
            595                 600                 605

Asp Gly Pro Ala Tyr Ile Leu Gly Gln Leu Cys Leu Ala Tyr Cys Pro
    610                 615                 620

Pro Arg Phe Phe Asn His Thr Arg Leu Val Thr Ala Gly Pro Gly His
625                 630                 635                 640

Thr Ala Ala Pro Ala Leu Arg Val Cys Ser Ser Cys His Ala Ser Cys
                645                 650                 655

Tyr Thr Cys Arg Gly Gly Ser Pro Arg Asp Cys Thr Ser Cys Pro Pro
            660                 665                 670

Ser Ser Thr Leu Asp Gln Gln Gln Gly Ser Cys Met Gly Pro Thr Thr
    675                 680                 685

Pro Asp Ser Arg Pro Arg Leu Arg Ala Ala Cys Pro His His Arg
    690                 695                 700

Cys Pro Ala Ser Ala Met Val Leu Ser Leu Leu Ala Val Thr Leu Gly
705                 710                 715                 720

Gly Pro Val Leu Cys Gly Met Ser Met Asp Leu Pro Leu Tyr Ala Trp
```

```
                        725                 730                 735
Leu Ser Arg Ala Arg Ala Thr Pro Thr Lys Pro Gln Val Trp Leu Pro
                740                 745                 750
Ala Gly Thr
        755

<210> SEQ ID NO 23
<211> LENGTH: 969
<212> TYPE: PRT
<213> ORGANISM: Homo sapiens

<400> SEQUENCE: 23

Met Pro Pro Arg Ala Pro Ala Pro Gly Pro Arg Pro Pro Arg
1               5                   10                  15

Ala Ala Ala Ala Thr Asp Thr Ala Gly Ala Gly Gly Ala Gly Gly
                20                  25                  30

Ala Gly Gly Ala Gly Gly Pro Gly Phe Arg Pro Leu Ala Pro Arg Pro
                35                  40                  45

Trp Arg Trp Leu Leu Leu Ala Leu Pro Ala Ala Cys Ser Ala Pro
        50                  55                  60

Pro Pro Arg Pro Val Tyr Thr Asn His Trp Ala Val Gln Val Leu Gly
65                  70                  75                  80

Gly Pro Ala Glu Ala Asp Arg Val Ala Ala His Gly Tyr Leu Asn
                85                  90                  95

Leu Gly Gln Ile Gly Asn Leu Glu Asp Tyr Tyr His Phe Tyr His Ser
                100                 105                 110

Lys Thr Phe Lys Arg Ser Thr Leu Ser Ser Arg Gly Pro His Thr Phe
            115                 120                 125

Leu Arg Met Asp Pro Gln Val Lys Trp Leu Gln Gln Glu Val Lys
        130                 135                 140

Arg Arg Val Lys Arg Gln Val Arg Ser Asp Pro Gln Ala Leu Tyr Phe
145                 150                 155                 160

Asn Asp Pro Ile Trp Ser Asn Met Trp Tyr Leu His Cys Gly Asp Lys
                165                 170                 175

Asn Ser Arg Cys Arg Ser Glu Met Asn Val Gln Ala Ala Trp Lys Arg
            180                 185                 190

Gly Tyr Thr Gly Lys Asn Val Val Val Thr Ile Leu Asp Asp Gly Ile
        195                 200                 205

Glu Arg Asn His Pro Asp Leu Ala Pro Asn Tyr Asp Ser Tyr Ala Ser
210                 215                 220

Tyr Asp Val Asn Gly Asn Asp Tyr Asp Pro Ser Pro Arg Tyr Asp Ala
225                 230                 235                 240

Ser Asn Glu Asn Lys His Gly Thr Arg Cys Ala Gly Glu Val Ala Ala
                245                 250                 255

Ser Ala Asn Asn Ser Tyr Cys Ile Val Gly Ile Ala Tyr Asn Ala Lys
            260                 265                 270

Ile Gly Gly Ile Arg Met Leu Asp Gly Asp Val Thr Asp Val Val Glu
        275                 280                 285

Ala Lys Ser Leu Gly Ile Arg Pro Asn Tyr Ile Asp Ile Tyr Ser Ala
290                 295                 300

Ser Trp Gly Pro Asp Asp Asp Gly Lys Thr Val Asp Gly Pro Gly Arg
305                 310                 315                 320

Leu Ala Lys Gln Ala Phe Glu Tyr Gly Ile Lys Lys Gly Arg Gln Gly
                325                 330                 335

Leu Gly Ser Ile Phe Val Trp Ala Ser Gly Asn Gly Gly Arg Glu Gly
```

-continued

```
                340             345                 350
Asp Tyr Cys Ser Cys Asp Gly Tyr Thr Asn Ser Ile Tyr Thr Ile Ser
            355                 360                 365
Val Ser Ser Ala Thr Glu Asn Gly Tyr Lys Pro Trp Tyr Leu Glu Glu
        370                 375                 380
Cys Ala Ser Thr Leu Ala Thr Thr Tyr Ser Ser Gly Ala Phe Tyr Glu
385                 390                 395                 400
Arg Lys Ile Val Thr Thr Asp Leu Arg Gln Arg Cys Thr Asp Gly His
                405                 410                 415
Thr Gly Thr Ser Val Ser Ala Pro Met Val Ala Gly Ile Ile Ala Leu
            420                 425                 430
Ala Leu Glu Ala Asn Ser Gln Leu Thr Trp Arg Asp Val Gln His Leu
        435                 440                 445
Leu Val Lys Thr Ser Arg Pro Ala His Leu Lys Ala Ser Asp Trp Lys
    450                 455                 460
Val Asn Gly Ala Gly His Lys Val Ser His Phe Tyr Gly Phe Gly Leu
465                 470                 475                 480
Val Asp Ala Glu Ala Leu Val Val Glu Ala Lys Lys Trp Thr Ala Val
                485                 490                 495
Pro Ser Gln His Met Cys Val Ala Ala Ser Asp Lys Arg Pro Arg Ser
            500                 505                 510
Ile Pro Leu Val Gln Val Leu Arg Thr Thr Ala Leu Thr Ser Ala Cys
        515                 520                 525
Ala Glu His Ser Asp Gln Arg Val Val Tyr Leu Glu His Val Val Val
    530                 535                 540
Arg Thr Ser Ile Ser His Pro Arg Arg Gly Asp Leu Gln Ile Tyr Leu
545                 550                 555                 560
Val Ser Pro Ser Gly Thr Lys Ser Gln Leu Leu Ala Lys Arg Leu Leu
                565                 570                 575
Asp Leu Ser Asn Glu Gly Phe Thr Asn Trp Glu Phe Met Thr Val His
            580                 585                 590
Cys Trp Gly Glu Lys Ala Glu Gly Gln Trp Thr Leu Glu Ile Gln Asp
        595                 600                 605
Leu Pro Ser Gln Val Arg Asn Pro Glu Lys Gln Gly Lys Leu Lys Glu
    610                 615                 620
Trp Ser Leu Ile Leu Tyr Gly Thr Ala Glu His Pro Tyr His Thr Phe
625                 630                 635                 640
Ser Ala His Gln Ser Arg Ser Arg Met Leu Glu Leu Ser Ala Pro Glu
                645                 650                 655
Leu Glu Pro Pro Lys Ala Ala Leu Ser Pro Ser Gln Val Glu Val Pro
            660                 665                 670
Glu Asp Glu Glu Asp Tyr Thr Ala Gln Ser Thr Pro Gly Ser Ala Asn
        675                 680                 685
Ile Leu Gln Thr Ser Val Cys His Pro Glu Cys Gly Asp Lys Gly Cys
    690                 695                 700
Asp Gly Pro Asn Ala Asp Gln Cys Leu Asn Cys Val His Phe Ser Leu
705                 710                 715                 720
Gly Ser Val Lys Thr Ser Arg Lys Cys Val Ser Val Cys Pro Leu Gly
                725                 730                 735
Tyr Phe Gly Asp Thr Ala Ala Arg Arg Cys Arg Arg Cys His Lys Gly
            740                 745                 750
Cys Glu Thr Cys Ser Ser Arg Ala Ala Thr Gln Cys Leu Ser Cys Arg
        755                 760                 765
```

-continued

```
Arg Gly Phe Tyr His His Gln Glu Met Asn Thr Cys Val Thr Leu Cys
        770                 775                 780
Pro Ala Gly Phe Tyr Ala Asp Glu Ser Gln Lys Asn Cys Leu Lys Cys
785                 790                 795                 800
His Pro Ser Cys Lys Lys Cys Val Asp Glu Pro Glu Lys Cys Thr Val
                805                 810                 815
Cys Lys Glu Gly Phe Ser Leu Ala Arg Gly Ser Cys Ile Pro Asp Cys
            820                 825                 830
Glu Pro Gly Thr Tyr Phe Asp Ser Glu Leu Ile Arg Cys Gly Glu Cys
        835                 840                 845
His His Thr Cys Gly Thr Cys Val Gly Pro Gly Arg Glu Glu Cys Ile
    850                 855                 860
His Cys Ala Lys Asn Phe His Phe His Asp Trp Lys Cys Val Pro Ala
865                 870                 875                 880
Cys Gly Glu Gly Phe Tyr Pro Glu Glu Met Pro Gly Leu Pro His Lys
                885                 890                 895
Val Cys Arg Arg Cys Asp Glu Asn Cys Leu Ser Cys Ala Gly Ser Ser
            900                 905                 910
Arg Asn Cys Ser Arg Cys Lys Thr Gly Phe Thr Gln Leu Gly Thr Ser
        915                 920                 925
Cys Ile Thr Asn His Thr Cys Ser Asn Ala Asp Glu Thr Phe Cys Glu
    930                 935                 940
Met Val Lys Ser Asn Arg Leu Cys Glu Arg Lys Leu Phe Ile Gln Phe
945                 950                 955                 960
Cys Cys Arg Thr Cys Leu Leu Ala Gly
                965
```

<210> SEQ ID NO 24
<211> LENGTH: 4403
<212> TYPE: DNA
<213> ORGANISM: Homo sapiens

<400> SEQUENCE: 24

```
cgggaacgcg ccgcggccgc ctcctcctcc ccggctcccg cccgcggcgg tgttggcggc      60
ggcggtggcg gcggcggcgg cgcttccccg gcgcggagcg gctttaaaag gcggcactcc     120
accccccggc gcactcgcag ctcgggcgcc gcgcgagcct gtcgccgcta tgcctccgcg     180
cgcgccgcct gcgcccgggc cccggccgcc gcccgggcc gccgccgcca ccgacaccgc      240
cgcgggcgcg gggggcgcgg ggggcgcggg gggcgccggc gggccgggt tccggccgct      300
cgcgccgcgt ccctggcgct ggctgctgct gctggcgctg cctgccgcct gctccgcgcc      360
cccgccgcgc cccgtctaca ccaaccactg ggcggtgcaa gtgctgggcg gcccggccga     420
ggcggaccgc gtggcggcgg cgcacggcta cctcaacttg ggccagattg gaaacctgga     480
agattactac cattttttatc acagcaaaac ctttaaaaga tcaaccttga gtagcagagg     540
ccctcacacc ttcctcagaa tggaccccca ggtgaaatgg ctccagcaac aggaagtgaa     600
acgaagggtg aagagacagg tgcgaagtga cccgcaggcc ctttacttca acgaccccat     660
ttggtccaac atgtggtacc tgcattgtgg cgacaagaac agtcgctgcc ggtcggaaat     720
gaatgtccag gcagcgtgga gaggggcta cacaggaaaa aacgtggtgg tcaccatcct     780
tgatgatggc atagagagaa atcaccctga cctggcccca aattatgatt cctacgccag     840
ctacgacgtg aacggcaatg attatgaccc atctccacga tatgatgcca gcaatgaaaa     900
taaacacggc actcgttgtg cgggagaagt tgctgcttca gcaaacaatt cctactgcat     960
cgtgggcata gcgtacaatg ccaaaatagg aggcatccgc atgctggacg gcgatgtcac    1020
```

```
agatgtggtc gaggcaaagt cgctgggcat cagacccaac tacatcgaca tttacagtgc    1080
cagctggggg ccggacgacg acggcaagac ggtggacggg cccggccgac tggctaagca    1140
ggctttcgag tatggcatta aaaagggccg gcagggcctg ggctccatt tcgtctgggc     1200 atctgggaat ggcgggagag aggggggacta ctgctcgtgc gatggctaca ccaacagcat   1260
ctacaccatc tccgtcagca cgccaccga gaatggctac aagccctggt acctggaaga    1320
gtgtgcctcc accctggcca ccacctacag cagtggggcc ttttatgagc gaaaaatcgt   1380
caccacggat ctgcgtcagc gctgtaccga tggccacact gggacctcag tctctgcccc   1440
catggtggcg ggcatcatcg ccttggctct agaagcaaac agccagttaa cctggaggga   1500
cgtccagcac ctgctagtga agacatcccg gccggcccac ctgaaagcga gcgactggaa   1560
agtaaacggc gcgggtcata agttagcca tttctatgga tttggtttgg tggacgcaga    1620
agctctcgtt gtggaggcaa agaagtggac agcagtgcca tcgcagcaca tgtgtgtggc   1680
cgcctcggac aagagaccca ggagcatccc cttagtgcag gtgctgcgga ctacggccct   1740
gaccagcgcc tgcgcggagc actcggacca gcgggtggtc tacttggagc acgtggtggt   1800
tcgcacctcc atctcacacc cacgccgagg agacctccag atctacctgg tttctccctc   1860
gggaaccaag tctcaacttt tggcaaagag gttgctggat cttccaatg aagggtttac     1920 aaactgggaa ttcatgactg tccactgctg gggagaaaag gctgaaggc agtggacctt    1980 ggaaatccaa gatctgccat cccaggtccg caacccggag aagcaaggga gttgaaaga    2040 atggagcctc atactgtatg gcacagcaga gcacccgtac cacaccttca gtgcccatca   2100
gtcccgctcg cggatgctgg agctctcagc cccagagctg gagccaccca aggctgccct   2160
gtcaccctcc caggtggaag ttcctgaaga tgaggaagat tacacagctc aatccacccc   2220
aggctctgct aatattttac agaccagtgt gtgccatccg gagtgtggtg acaaaggctg   2280
tgatggcccc aatgcagacc agtgcttgaa ctgcgtccac ttcagcctgg ggagtgtcaa   2340
gaccagcagg aagtgcgtga gtgtgtgccc cttgggctac tttggggaca cagcagcaag   2400
acgctgtcgc cggtgccaca aggggtgtga gacctgctcc agcagagctg cgacgcagtg   2460
cctgtcttgc cgccgcgggt ctatcaccca caggagatg aacacctgtg tgaccctctg    2520
tcctgcagga ttttatgctg atgaaagtca gaaaaattgc cttaaatgcc acccaagctg   2580
taaaaagtgc gtggatgaac ctgagaaatg tactgtctgt aaagaaggat tcagccttgc   2640
acggggcagc tgcattcctg actgtgagcc aggcacctac tttgactcag agctgatcag   2700
atgtggggaa tgccatcaca cctgcggaac ctgcgtgggg ccaggcagag aagagtgcat   2760
tcactgtgcg aaaaacttcc acttccacga ctggaagtgt gtgccagcct gtggtgaggg   2820
cttctaccca gaagagatgc cgggcttgcc ccacaaagtg tgtcgaaggt gtgacgagaa   2880
ctgcttgagc tgtgcaggct ccagcaggaa ctgtagcagg tgtaagacgg gcttcacaca    2940 gctgggacc tcctgcatca ccaaccacac gtgcagcaac gctgacgaga cattctgcga    3000
gatggtgaag tccaaccggc tgtgcgaacg gaagctcttc attcagttct gctgccgcac   3060
gtgcctcctg gccgggtaag ggtgcctagc tgcccacaga gggcaggcac tcccatccat   3120
ccatccgtcc accttcctcc agactgtcgg ccagagtctg tttcaggagc ggcgccctgc   3180
acctgacagc tttatctccc caggagcagc atctctgagc acccaagcca ggtgggtggt   3240
ggctcttaag gaggtgttcc taaaatggtg atatcctctc aaatgctgct tgttggctcc   3300
agtcttccga caaactaaca ggaacaaaat gaattctggg aatccacagc tctggctttg   3360
gagcagcttc tgggaccata agtttactga atcttcaaga ccaaagcaga aaagaaaggc   3420
```

```
gcttggcatc acacatcact cttctccccg tgcttttctg cggctgtgta gtaaatctcc    3480
ccggcccagc tggcgaaccc tgggccatcc tcacatgtga caaagggcca gcagtctacc    3540
tgctcgttgc ctgccactga gcagtctggg gacggtttgg tcagactata aataagatag    3600
gtttgagggc ataaaatgta tgaccactgg ggccggagta tctatttcta catagtcagc    3660
tacttctgaa actgcagcag tggcttagaa agtccaattc caaagccaga ccagaagatt    3720
ctatcccccg cagcgctctc ctttgagcaa gccgagctct ccttgttacc gtgttctgtc    3780
tgtgtcttca ggagtctcat ggcctgaacg accacctcga cctgatgcag agccttctga    3840
ggagaggcaa caggaggcat tctgtggcca gccaaaaggt accccgatgg ccaagcaatt    3900
cctctgaaca aaatgtaaag ccagccatgc attgttaatc atccatcact tcccatttta    3960
tggaattgct tttaaaatac atttggcctc tgcccttcag aagactcgtt tttaaggtgg    4020
aaactcctgt gtctgtgtat attacaagcc tacatgacac agttggattt attctgccaa    4080
acctgtgtag gcattttata agctacatgt tctaattttt accgatgtta attattttga    4140
caaatatttc atatattttc attgaaatgc acagatctgc ttgatcaatt cccttgaata    4200
gggaagtaac atttgcctta aatttttcg acctcgtctt tctccatatt gtcctgctcc      4260
cctgtttgac gacagtgcat ttgccttgtc acctgtgagc tggagagaac ccagatgttg    4320
tttattgaat ctacaactct gaaagagaaa tcaatgaagc aagtacaatg ttaacccctaa    4380 attaataaaa gagttaacat ccc                                             4403

<210> SEQ ID NO 25
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ccgggagaga agtctcctct gcattctcga gaatgcagag gagacttctc tcttttttg          58

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ccggcctaga gaacaagggc tactactcga gtagtagccc ttgttctcta ggttttttg          58

<210> SEQ ID NO 27
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ccggaggcta acaacactgg gtcttctcga gaagacccag ttgttgtagc ctttttttg          58

<210> SEQ ID NO 28
<211> LENGTH: 58
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 28
ccggcctccc actatacgcc tggctctcga gagccaggcg tatagtggga ggtttttg         58

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccggcccttg acgtcagca ctgaactcga gttcagtgct gacgtccaag ggtttttg         58

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AMC (amino-methyl-coumarin)

<400> SEQUENCE: 30

Arg Thr Lys Arg Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-amino octanoyl

<400> SEQUENCE: 31

Xaa Leu Leu Leu Leu Arg Val Lys Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 11-amino undecanoyl

<400> SEQUENCE: 32

Xaa Leu Leu Leu Leu Arg Val Lys Arg
1               5

<210> SEQ ID NO 33
<211> LENGTH: 6
<212> TYPE: PRT
<213> ORGANISM: Artificial Sequence
<220> FEATURE:

-continued

<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: AMC (methyl-coumaryl-7-amide)

<400> SEQUENCE: 33

Glu Arg Val Lys Arg Xaa
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AMC (methyl-coumaryl-7-amide)

<400> SEQUENCE: 34

Arg Thr Lys Arg Xaa
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 35

Xaa Xaa Xaa Xaa Arg Xaa Xaa Arg
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any positively charged amino acid or

```
       stereoisomer thereof
<220>  FEATURE:
<221>  NAME/KEY: MISC_FEATURE
<222>  LOCATION: (1)..(4)
<223>  OTHER INFORMATION: This region may or may not be present and may
       or may not be N-term acylated
<220>  FEATURE:
<221>  NAME/KEY: MOD_RES
<222>  LOCATION: (6)..(7)
<223>  OTHER INFORMATION: Any amino acid or stereoisomer thereof
<220>  FEATURE:
<221>  NAME/KEY: MOD_RES
<222>  LOCATION: (8)..(8)
<223>  OTHER INFORMATION: Arginine, arginine derivative, arginine mimetic
       or a transition state analogue
<220>  FEATURE:
<223>  OTHER INFORMATION: See specification as filed for detailed
       description of substitutions and preferred embodiments

<400>  SEQUENCE: 36

Xaa Xaa Xaa Xaa Arg Xaa Xaa Arg
1               5

<210>  SEQ ID NO 37
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide
<220>  FEATURE:
<221>  NAME/KEY: MOD_RES
<222>  LOCATION: (1)..(4)
<223>  OTHER INFORMATION: Any amino acid with a hydrophobicity score
       between about 4.5 to -0.4 based on a Kyte-Doolittle hydrophobicity
       plot, Lys, His or Arg and is not an aromatic or negatively charged
       amino acid
<220>  FEATURE:
<221>  NAME/KEY: MISC_FEATURE
<222>  LOCATION: (1)..(4)
<223>  OTHER INFORMATION: This region may or may not be present and may
       or may not be N-term acylated
<220>  FEATURE:
<221>  NAME/KEY: MOD_RES
<222>  LOCATION: (7)..(7)
<223>  OTHER INFORMATION: Any amino acid or stereoisomer thereof
<220>  FEATURE:
<221>  NAME/KEY: MOD_RES
<222>  LOCATION: (8)..(8)
<223>  OTHER INFORMATION: Arginine, arginine derivative, arginine mimetic
       or a transition state analogue
<220>  FEATURE:
<223>  OTHER INFORMATION: See specification as filed for detailed
       description of substitutions and preferred embodiments

<400>  SEQUENCE: 37

Xaa Xaa Xaa Xaa Arg Val Xaa Arg
1               5

<210>  SEQ ID NO 38
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide
<220>  FEATURE:
<221>  NAME/KEY: MOD_RES
<222>  LOCATION: (1)..(4)
<223>  OTHER INFORMATION: Any amino acid with a hydrophobicity score
       between about 4.5 to -0.4 based on a Kyte-Doolittle hydrophobicity
       plot, Lys, His or Arg and is not an aromatic or negatively charged
       amino acid
<220>  FEATURE:
<221>  NAME/KEY: MISC_FEATURE
<222>  LOCATION: (1)..(4)
```

```
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 38

Xaa Xaa Xaa Xaa Arg Xaa Xaa Arg
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any positively charged amino acid or
      stereoisomer thereof
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 39

Xaa Xaa Xaa Xaa Arg Xaa Xaa Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
```

```
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 40

Xaa Xaa Xaa Xaa Arg Val Xaa Arg
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 41

Xaa Xaa Xaa Xaa Arg Xaa Xaa Arg
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any positively charged amino acid or
      stereoisomer thereof
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
```

```
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 42

Xaa Xaa Xaa Xaa Arg Xaa Xaa Arg
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 43

Xaa Xaa Xaa Xaa Arg Val Xaa Arg
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
```

```
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 44

Xaa Xaa Xaa Xaa Arg Xaa Xaa Arg
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any positively charged amino acid or
      stereoisomer thereof
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 45

Xaa Xaa Xaa Xaa Arg Xaa Xaa Arg
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
```

```
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 46

Xaa Xaa Xaa Xaa Arg Val Xaa Arg
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 47

Xaa Xaa Xaa Xaa Arg Xaa Xaa Arg
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 48
```

Xaa Xaa Xaa Xaa Arg Xaa Xaa Arg
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 49

Xaa Xaa Xaa Xaa Arg Val Xaa Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 50

Xaa Xaa Xaa Xaa Arg Xaa Xaa Arg
1               5

<210> SEQ ID NO 51
<211> LENGTH: 8
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 51

Xaa Xaa Xaa Xaa Arg Xaa Xaa Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 52

Xaa Xaa Xaa Xaa Arg Val Xaa Arg
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
```

```
        or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
        or a transition state analogue
<220> FEATURE:
<223> OTHER INFORMATION: See specification as filed for detailed
        description of substitutions and preferred embodiments

<400> SEQUENCE: 53

Xaa Xaa Xaa Xaa Arg Xaa Xaa Arg
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
        or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
        or a transition state analogue
<220> FEATURE:
<223> OTHER INFORMATION: See specification as filed for detailed
        description of substitutions and preferred embodiments

<400> SEQUENCE: 54

Xaa Xaa Xaa Xaa Arg Xaa Xaa Arg
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
        or may not be N-term acylated
<220> FEATURE:
```

```
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 55

Xaa Xaa Xaa Xaa Arg Val Xaa Arg
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 56

Xaa Xaa Xaa Xaa Arg Xaa Xaa Arg
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
```

-continued

```
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 57

Xaa Xaa Xaa Xaa Arg Xaa Xaa Arg
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic hydrophobic amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 58

Xaa Xaa Xaa Xaa Arg Val Xaa Arg
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments
```

```
<400> SEQUENCE: 59

Xaa Xaa Xaa Xaa Arg Xaa Xaa Arg
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 60

Xaa Xaa Xaa Xaa Arg Xaa Xaa Arg
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 61

Xaa Xaa Xaa Xaa Arg Val Xaa Arg
1               5

<210> SEQ ID NO 62
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 62

Xaa Xaa Xaa Xaa Arg Xaa Xaa Arg
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 63

Xaa Xaa Xaa Xaa Arg Xaa Xaa Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
```

```
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 64

Xaa Xaa Xaa Xaa Arg Val Xaa Arg
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 65

Xaa Xaa Xaa Xaa Arg Xaa Xaa Arg
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
```

```
-continued

<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 66

Xaa Xaa Xaa Xaa Arg Xaa Xaa Arg
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 67

Xaa Xaa Xaa Xaa Arg Val Xaa Arg
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
```

```
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 68

Xaa Xaa Xaa Xaa Arg Xaa Xaa Arg
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 69

Xaa Xaa Xaa Xaa Arg Xaa Xaa Arg
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Leu, Iso or Val
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments
```

```
<400> SEQUENCE: 70

Xaa Xaa Xaa Xaa Arg Val Xaa Arg
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 71

Leu Leu Leu Leu Arg Xaa Xaa Arg
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 72

Leu Leu Leu Leu Arg Xaa Xaa Arg
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
```

```
      or may not be N-term acylated
<220> FEATURE:
<221> NAME/KEY: MOD_RES
<222> LOCATION: (7)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 73

Leu Leu Leu Leu Arg Val Xaa Arg
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 74

Leu Leu Leu Leu Arg Xaa Xaa Arg
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 75

Leu Leu Leu Leu Arg Xaa Xaa Arg
1               5
```

```
<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 76

Leu Leu Leu Leu Arg Val Xaa Arg
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 77

Leu Leu Leu Leu Arg Xaa Xaa Arg
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
```

```
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a  transition state analogue
<220> FEATURE:
<223> OTHER INFORMATION: See specification as filed for detailed
      description of substitutions and preferred embodiments

<400> SEQUENCE: 78

Leu Leu Leu Leu Arg Xaa Xaa Arg
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 79

Leu Leu Leu Leu Arg Val Xaa Arg
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
```

```
<223> OTHER INFORMATION: See specification as filed for detailed
      description of substitutions and preferred embodiments

<400> SEQUENCE: 80

Leu Leu Leu Leu Arg Xaa Xaa Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 81

Leu Leu Leu Leu Arg Xaa Xaa Arg
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 82

Leu Leu Leu Leu Arg Val Xaa Arg
1               5

<210> SEQ ID NO 83
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 83

Leu Leu Leu Leu Arg Xaa Xaa Arg
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 84

Leu Leu Leu Leu Arg Xaa Xaa Arg
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed description of substitutions and preferred embodiments

<400> SEQUENCE: 85

Leu Leu Leu Leu Arg Val Xaa Arg
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 86

Leu Leu Leu Leu Arg Xaa Xaa Arg
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 87

Leu Leu Leu Leu Arg Xaa Xaa Arg
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)

```
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 88

Leu Leu Leu Leu Arg Val Xaa Arg
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 89

Leu Leu Leu Leu Arg Xaa Xaa Arg
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
```

```
      or a transition state analogue
<220> FEATURE:
<223> OTHER INFORMATION: See specification as filed for detailed
      description of substitutions and preferred embodiments

<400> SEQUENCE: 90

Leu Leu Leu Leu Arg Xaa Xaa Arg
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 91

Leu Leu Leu Leu Arg Val Xaa Arg
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 92

Leu Leu Leu Leu Arg Xaa Xaa Arg
1               5

<210> SEQ ID NO 93
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 93

Leu Leu Leu Leu Arg Xaa Xaa Arg
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 94

Leu Leu Leu Leu Arg Val Xaa Arg
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
```

```
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 95

Leu Leu Leu Leu Arg Xaa Xaa Arg
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 96

Leu Leu Leu Leu Arg Xaa Xaa Arg
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Any amino acid or stereoisomer thereof
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 97

Leu Leu Leu Leu Arg Val Xaa Arg
1               5

<210> SEQ ID NO 98
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 98

Leu Leu Leu Leu Arg Xaa Xaa Arg
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 99

Leu Leu Leu Leu Arg Xaa Xaa Arg
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
```

-continued

<223> OTHER INFORMATION: See specification as filed for detailed
      description of substitutions and preferred embodiments

<400> SEQUENCE: 100

Leu Leu Leu Leu Arg Val Xaa Arg
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 101

Leu Leu Leu Leu Arg Xaa Xaa Arg
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Any amino acid or stereoisomer thereof
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 102

Leu Leu Leu Leu Arg Xaa Xaa Arg
1               5

<210> SEQ ID NO 103

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 103

Leu Leu Leu Leu Arg Val Xaa Arg
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 104

Leu Leu Leu Leu Arg Xaa Xaa Arg
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(6)
```

```
<223> OTHER INFORMATION: Gly or Ala
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 105

Leu Leu Leu Leu Arg Xaa Xaa Arg
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 106

Leu Leu Leu Leu Arg Val Xaa Arg
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any small amino acid
<220> FEATURE:
<221> NAME/KEY: MOD_RES
<222> LOCATION: (3)..(4)
<223> OTHER INFORMATION: Any amino acid with a hydrophobicity score
      between about 4.5 to -0.4 based on a Kyte-Doolittle hydrophobicity
      plot, Lys, His or Arg and is not an aromatic or negatively charged
      amino acid
<220> FEATURE:
<221> NAME/KEY: MISC_FEATURE
<222> LOCATION: (1)..(4)
<223> OTHER INFORMATION: This region may or may not be present and may
      or may not be N-term acylated
<220> FEATURE:
<221> NAME/KEY: MOD_RES
<222> LOCATION: (6)..(7)
<223> OTHER INFORMATION: Any amino acid or stereoisomer thereof
<220> FEATURE:
<221> NAME/KEY: MOD_RES
```

```
<222> LOCATION: (8)..(8)
<223> OTHER INFORMATION: Arginine, arginine derivative, arginine mimetic
      or a transition state analogue
<220> FEATURE:
<223> OTHER INFORMATION: See specification as filed for detailed
      description of substitutions and preferred embodiments

<400> SEQUENCE: 107

Xaa Xaa Xaa Xaa Arg Xaa Xaa Arg
1               5
```

MULTI-LEU PEPTIDES AND ANALOGUES THEREOF AS SELECTIVE PACE4 INHIBITORS AND EFFECTIVE ANTIPROLIFERATIVE AGENTS

CROSS REFERENCE TO RELATED APPLICATION

This application is the national stage entry of International Patent Application No. PCT/CA2009/000935 having International Publication Number WO. 2010/003231 A1 and an international filing date of Jul. 6, 2009, which claims filing benefit of U.S. Provisional Patent Application Ser. No. 61/079,820 having a filing date of Jul. 11, 2008.

SEQUENCE LISTING

The instant application contains a Sequence Listing which has been submitted in ASCII format via EFS-Web and is hereby incorporated by reference in its entirety. Said ASCII copy, created on Feb. 4, 2011, is named OGILPCTU.txt and is 109,336 bytes in size.

TECHNICAL FIELD

The present invention relates to PACE4 inhibitors and their uses for limiting the proliferation of a cell.

BACKGROUND OF THE INVENTION

Cancer cells are characterized by multiple genetic alterations that confer physiological changes, leading to uncontrolled division and ability to invade other tissues. These acquired capabilities, namely self-sufficiency in growth signals, insensitivity to growth-inhibitory signals, evasion of programmed cell death, limitless replicative potential, sustained angiogenesis, tissue invasion and metastasis are essential for malignant growth. Recent studies have associated the family of enzymes known as the proprotein convertases (PCs) to cancer (Bassi et al., 2005, Mol. Carcinog., 44: 151-161; Khatib et al., 2002, Am. J. Pathol., 160: 1921-1935). PCs are serine proteases that optimally cleave substrates at R—X—K/R—R motif. These processing events, resulting in the activation of protein precursors, occur at multiple levels of cell secretory pathways, and even at the cell surface.

In mammalian cells, seven members of this family have been identified: furin, PACE4, PC1/3, PC2, PC4, PC5/6 and PC7, with differential expression in tissues, ranging from ubiquitous (eg. furin) to an endocrine restricted expression (PC1/3 and PC2).

The association of PCs with cancer was firstly done by comparative studies of normal and cancerous cells showing higher expression of PCs in small cell lung cancer (Clark et al., 1993, Peptides, 14: 1021-1028), non-small cell lung carcinoma (Mbikay et al., 1997, Cancer, 75: 1509-1514), breast (Cheng et al., 1997, Int. J. Cancer, 71: 966-971), colon (Tzimas et al., 2005, BMC Cancer, 5: 149), and head and neck (Bassi et al., Mol. Carcinog., 31: 224-232) tumors cells. A correlation between expression of some PCs, namely furin and PACE4, and tumor cell aggressiveness has been established for different cell types. It as been demonstrated that the overexpression of PACE4 in non-malignant keratinocyte cell lines renders these cells malignant. Non-selective inhibitors that target several PCs together (such as furin, PACE4 and PC5/6 together) have been described (Bassi et al., 2005, Cancer Res., 65: 7310-7319; Mahloogi et al., 2002, Carcinogenesis, 23: 565-572; Bassi et al., 2000, Mol. Carcinog., 28: 63-69; Hubbard et al., 1997, Cancer Res., 57: 5226-5231).

Moreover, it has been proposed that PC activity regulates epithelial cell differentiation in a prostate cancer cell line. One possible mechanism underlying these observations could be on the basis of the precursors activation by overexpressed PCs. Thus, it is hypothesized that aberrant processing events provide cancer cells a higher capacity to (i) remodel the extracellular; (ii) to interact with their host micro-environment to favor tumor cell adhesion and; (iii) to modulate their proliferation and differentiation. Alternatively, PC's overexpression is required to sustain these pathophysiological functions to maintain cancer cells immortality The situation becomes more complex as the expression/activity of PCs are modulated differently in various cancer cells or cancer models. If one wishes to understand the specific contribution of each PC in tumorigenesis, the necessity for potent, specific and cell effective inhibitors, either pharmacologic or molecular, for each member of this enzyme family is crucial. Until now, these pharmacological tools are limited and lack specificity for single PCs.

It would be highly desirable to be provided with selective PCs inhibitors. It would also be highly desirable to be provided with selective PCs inhibitors that are effective in treating cancer. More specifically, it would be highly desirable to be provided with selective PCs inhibitors that have antiproliferative effects.

SUMMARY OF THE INVENTION

In accordance with the present invention there is now provided PACE4 inhibitors and their uses for limiting the proliferation of a cell.

According to one aspect of the present invention, there is provided a PACE4 inhibitor comprising a peptide sequence consisting of the following formula:

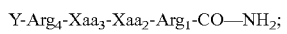

$Y\text{-}Arg_4\text{-}Xaa_3\text{-}Xaa_2\text{-}Arg_1\text{-}CO\text{---}NH_2$;

wherein $Arg_1$ is an arginine, arginine derivative, arginine mimetic or a transition state analogue;

$Xaa_2$ and $Xaa_3$ are any amino acids or stereoisomers thereof; and

Y is absent or comprises the formula $Z\text{-}Xaa_8\text{-}Xaa_7\text{-}Xaa_6\text{-}Xaa_5$, wherein $Xaa_5$, $Xaa_6$, $Xaa_7$ and $Xaa_8$ have an hydrophobicity score between about 4.5 to −0.4 based on a Kyte-Doolittle hydrophobicity plot, or $Xaa_5$, $Xaa_6$, $Xaa_7$ and $Xaa_8$ are independently selected from the group consisting of Lys, His and Arg;

Z is absent or comprises an N-terminal acyl group linked to the N-terminal of the peptide sequence;

with the proviso that $Xaa_5$, $Xaa_6$, $Xaa_7$ and $Xaa_8$ are not aromatic or negatively charged amino acids.

Particularly, $Xaa_5$, $Xaa_6$, $Xaa_7$ and $Xaa_8$ are positively charged amino acids or stereoisomers thereof. More preferably, $Xaa_3$ is Val. Preferably, $Xaa_2$ and $Xaa_3$ are independently selected from of Gly and Ala. More preferably, $Xaa_2$ is Lys or Arg or an analogue thereof.

In a particular embodiment, $Xaa_5$, $Xaa_6$, $Xaa_7$ and $Xaa_8$ are Leu.

In an embodiment, $Xaa_5$, $Xaa_6$, $Xaa_7$ and $Xaa_8$ are aliphatic hydrophobic amino acids, such as Leu, Iso or Val.

In another embodiment, $Xaa_7$ and $Xaa_8$ are small amino acids.

In a particular embodiment, the N terminus of the inhibitor is acylated (e.g. acetylated). Further, the N terminus acylation is with fatty omega amino acids or with steroid derivatives.

The fatty omega amino acids can be C2 to C18, preferably C2 to C11, more preferably the fatty omega amino acids are selected from the group consisting of 11-amino undecanoyl, 8-amino octanoyl and the steroid derivatives are cholyl.

In another embodiment, the inhibitor comprises at least one of the following amino acid sequences: SEQ ID NO: 2, 3, 4, 5, 6 and 7.

According to another aspect of the present invention, there is provided a composition comprising the PACE4 inhibitor as defined herein and a carrier.

In another embodiment, the composition further comprises at least one anti-cancer drug.

Preferably, the composition is adapted for delivery by at least one of the following route selected from the group consisting of oral, mucosal, intranasal, intraocular, intratracheal, intrabronchial, intrapleural, intraperitoneal, intracranial, intramuscular, intravenous, intraarterial, intralymphatic, subcutaneous, intratumoral, gastric, enteral, colonic, rectal, urethral and intravesical route.

According to still another aspect of the present invention, there is provided a method of lowering PACE4 activity in a cell, comprising contacting the PACE4 inhibitor or the composition as defined herein with the cell, thereby lowering PACE4 activity in the cell.

According to yet another aspect of the present invention, there is provided a method of reducing the proliferation of a cell in a subject, comprising administering the PACE4 inhibitor or the composition as defined herein to the subject, thereby reducing the proliferation of the cell in the subject.

According to a further aspect of the present invention, there is provided a method of reducing tumor growth in a subject, comprising administering the PACE4 inhibitor or the composition as defined herein to the subject, thereby reducing tumor growth in the subject.

According to yet a further aspect of the present invention, there is provided a method for the prophylaxis or treatment of a cancer in a subject, comprising administering to said subject a therapeutically effective amount of the PACE4 inhibitor or the composition as defined herein, thereby preventing or treating the cancer in the subject.

Preferably, the cell is in a subject. More preferably, the cell is a cancer cell. More preferably, the cell has increased PACE4 activity.

According to still a further aspect of the present invention, there is provided the use of the PACE4 inhibitor or the composition as defined herein in the manufacture of a medicament for preventing or treating cancer in a subject.

According to another aspect of the present invention, there is provided the use of the PACE4 inhibitor or the composition as defined herein for preventing or treating cancer in a subject.

More specifically, the cancer is a prostate cancer or a metastasis thereof.

According to yet another aspect of the present invention, there is provided the use of the PACE4 inhibitor or the composition as defined herein for lowering PACE4 activity in a cell, for reducing proliferation of a cell in a subject, and for reducing tumor growth in a subject.

In a particular embodiment, the inhibitor or the composition reduces cell proliferation, tumor growth or metastasis formation.

In another embodiment, there is provided a method of screening for a PACE4 inhibitor comprising the steps of contacting an agent with a PACE4 protein; assessing the activity of the PACE4 protein, wherein a reduction of the activity of the PACE4 protein compared to the basal activity of the PACE4 protein that has not been in contact with the agent is indicative that the agent is an inhibitor of PACE4.

According to another aspect of the present invention, there is provided a method of identifying a cell proliferation inhibitor, comprising the steps of contacting an agent with a PACE4 protein in a cell; assessing the activity of the PACE4 protein, wherein a reduction of the activity of the PACE4 protein compared to the basal activity of the PACE4 protein that has been in contact with the agent is indicative that the agent is an inhibitor of PACE4 inhibiting cell proliferation.

In a further embodiment, the method further comprises the step of comparing the proliferation rate of the cell to a control cell not contacted with the agent.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION OF THE PREFERRED EMBODIMENT

Figure 1A:
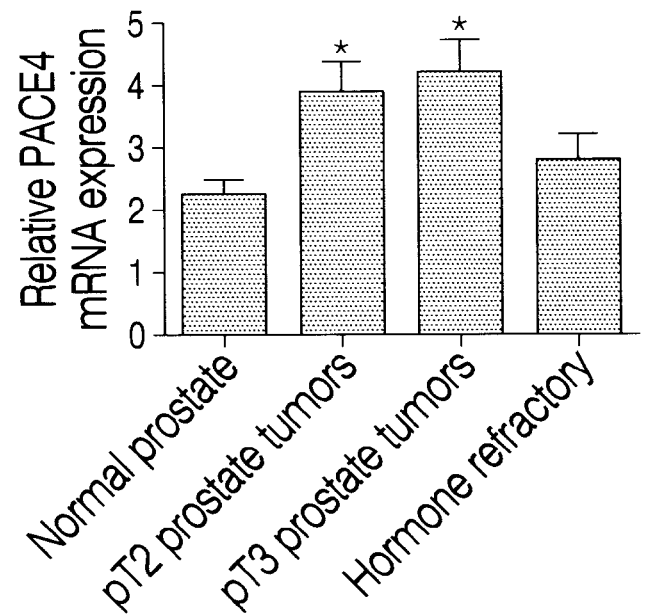
FIG. 1 illustrates the overexpression of PACE4 mRNA in prostate cancer as measured by (A) quantitative PCR and (B) in situ hybridization of normal prostate tissue shows PACE4 mRNA localized to epithelial cells lining the ducts, while in (C) tumor tissues PACE4 expression is widespread, disorganized and localized into the stroma. The (*) indicate that values are mean±SEM; *$P<0.05$.

The present application provides selective PACE4 inhibitors which have antiproliferative effects.

The relationship between the expression/activity of PCs and cancer has become stronger within the last few years. Since cancer cell lines generally express varying cocktail of PCs, it always remains unclear whether one PC is more important or whether the cell simply establish multiple PC overexpression to assure redundancy. It is disclosed herein that specific inhibition of a PC (e.g. PACE4 expression) in cancer (e.g. such as the cell line DU145) causes a reduction in cell proliferation and clonogenic capacity both in vitro and in vivo (e.g. as shown in FIGS. 3 and 4).

Therefore, the unavailability of potent and specific PC inhibitors represents a problem for the determination of the specific functions of overexpressed PCs in cancer cells. While the hypothesis of PCs importance in cancer has much credibility, studies with specific PC inhibitors are crucial, since each cancer cells overexpress multiple PCs. This variable PC expression pattern suggests that each PC can contributes differently to the apparition and the maintenance of given cancers and their specific functions have to be defined within each cancer cell.

Overexpression of PACE4 in different clinical stages prostate cancer tissues (FIG. 1) is disclosed herein. This result demonstrate the PACE4 specific contribution to prostate cancer, since other co-expressed PC (including furin and PC7) did not show significant variation in their expression levels.

To test the impact of PACE4 in overall tumor progression, the well-established model cell line, the DU145 epithelial-like cell line, derived from a human metastatic carcinoma of the prostate was used. These androgen non-responsive cells are tumorigenic in nude mice forming adenocarcinoma (grade II) consistent with prostatic primary tumors.

Targeted inhibition studies in tumoral cell lines with endogenously high expression levels of PCs are useful to understand the specific contribution of these enzymes into the generation of cancer related proteins, although functional redundancy might be observed for some substrates.

A stable DU145 cell line in which the expression of PACE4 would be silenced or significantly reduced was also established. A delta ribozyme (δRz) technology was used to accomplish this, the new δRz generation harboring a biosensor module that activates the molecule only in the presence of the appropriate RNA target substrate. A specific on/off adapter (SOFA module) gives a higher specificity of the δRz toward its target, but also a higher cleavage capacity.

The expression vector used in this study produced a chimeric RNA transcript constituted of a tRNA$^{Val}$ motif and the PACE4-SOFA-δRz. This molecule had the same cleavage capacity than the PACE4-SOFA-δRz itself by performing as observed in an in vitro cleavage assay performed transfecting DU145 cells.

After hygromycin selection, a very low number of stable cells were analyzed, since transfected DU145 cells grew very slowly. This is the consequence of lowered PACE4 level, thus arguing for the important role of this PC for DU145 cells proliferation. This link between PACE4 and cell proliferation could explain why no clones with a lower expression levels was obtained.

Figure 2A:
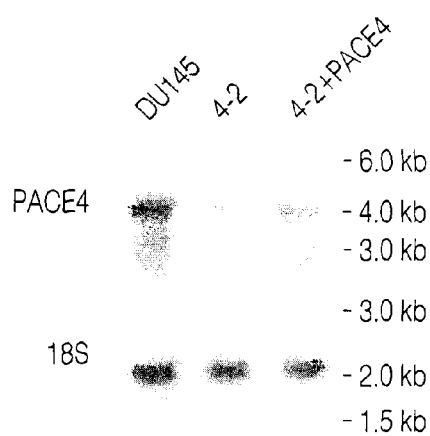
FIG. 2 illustrates expression of PACE4-SOFA-δRz vector transfected into the DU145 cell line, a highly invasive, androgen-independent prostate epithelial tumor cell line, (A) by Northern blot analysis on total RNA extracts performed from wild-type DU145 cell line (DU145), on DU145 cells transfected with ptRNAVal-PACE4-SOFA-δRz (4-2) and, on DU145 cells transfected with ptRNAVal-PACE4-SOFA-δRz and co-transfected with PACE4 cDNA expression vector (4-2+PACE4). In (B), a densitometric analysis using 18S ribosomal RNA as loading control to quantify the mRNA levels in the cell line illustrated in (A) is shown. The Northern blot analysis of mRNA levels of two others endogenous expressed PCs is shown and confirms the specificity of the PACE4-SOFA-δRz cleavage, wherein levels of (C) furin and (D) PC7 mRNAs remained mostly unchanged in the 4-2 cells, confirming the reduction of PACE4 expression without significantly affecting the expression of other endogenous PCs. The (*) indicates that values are mean±SEM (n=3); *$P<0.05$.
Figure 2C:
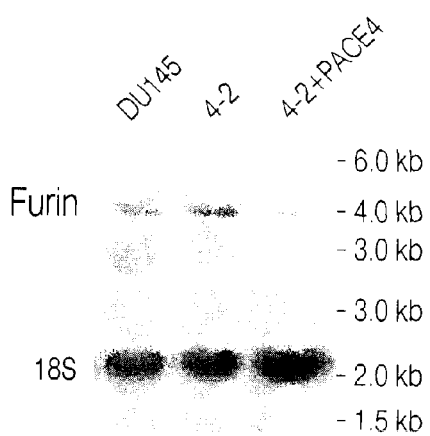
Figure 2B:
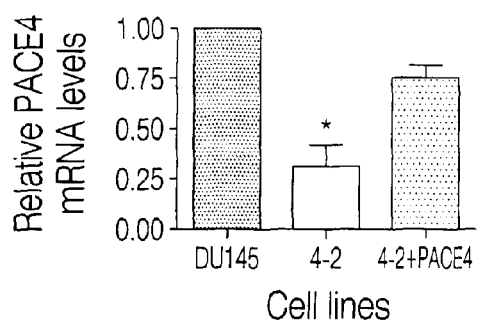
Figure 2D:
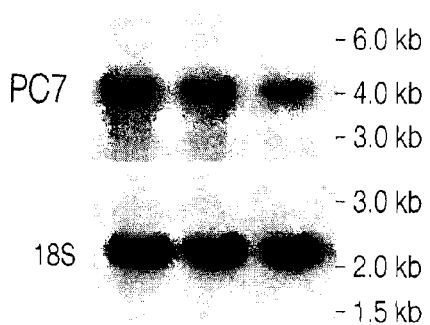

Considering the high specificity potential of PACE4-SOFA-δRz, the cell line with the lowest levels of PACE4 mRNA levels was chosen for further studies (see FIG. 2A). Northern blots performed for two other endogenous expressed PCs showed that this effect is specific to PACE4 (FIGS. 2C and 2D). The stable cell line was transfected with the SOFA-δRz expression vector and named 4-2, while the 4-2 cell line was stably transfected with the PACE4 expression vector and named 4-2+PACE4.

The consequences of lowered levels of PACE4 were well illustrated by the reduced cell proliferation rate and the incapacity of these cells to form subcutaneous tumors in nude mice (FIGS. 3 and 4). The restoration of PACE4 expression levels in this cell line allowed a partial recovery of the in vitro proliferation rate, demonstrating that PACE4 is a key player for tumoral growth and its levels have to be high to achieve this function.

The cell lines characterized in this study constitute important tools for the identification of cellular proteins processed by PACE4. The results obtained with conditioned media showed that PACE4 is important for the generation of secreted proliferation factors; but also showed that these cells had a lower capacity to react when exposed to conditioned media issued from untransfected cells.

One of the keys to the development of potent and selective PC inhibitors is an understanding of the substrate-binding pocket. The deepest region of the substrate-binding pocket accommodates the consensus motif RXKR (i.e. $P_4$-$P_3$-$P_2$-$P_1$) and is nearly identically in all PCs. Potency and selectivity are determined by a less deeper region that interacts with $P_8$-$P_7$-$P_6$-$P_5$ of the inhibitor peptide (see Henrich et al., 2005, J. Mol. Biol., 345: 211-227; Fugere and Day, 2005, Trends Pharmacol. Sci., 26: 294-301; Henrich et al., 2003, Nat. Struct. Biol., 10: 520-526).

Endogenous inhibitors are often a good starting point in the development of pharmacological compounds. For example, proSAAS and the 7B2 C-terminal peptide are two endogenous inhibitors identified that inhibit PC1/3 and PC2, respectively. PC pro-domains are autoprocessed in cis by their cognate PC, but remain bound to the active site through their C-terminal PC-recognition sequence until the complex reaches the compartment of zymogen activation. Thus, pro-domains are dual-function molecules, being the first substrate and first inhibitor encountered by PCs in cells.

The deepest region of the substrate-binding pocket accommodates the consensus motif RXKR ($P_4$-$P_3$-$P_2$-$P_1$) nearly identical in all PCs. Using an incremental peptide assay (IPA), the core warhead sequence, RVKR (SEQ ID NO: 1), was extended one amino acid at a time.

In a first aspect, it is provided a PACE4 inhibitor comprising a peptide sequence consisting of the following formula:

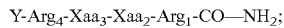

wherein

Arg$_1$ is an arginine, arginine derivative, arginine mimetic or a transition state analogue;

Xaa$_2$ and Xaa$_3$ are any amino acids or stereoisomers thereof; and

Y is absent or comprises the formula Z-Xaa$_8$-Xaa$_7$-Xaa$_6$-Xaa$_5$, wherein

Xaa$_5$, Xaa$_6$, Xaa$_7$ and Xaa$_8$ have an hydrophobicity score between about 4.5 to −0.4 based on a Kyte-Doolittle hydrophobicity plot, or Xaa$_5$, Xaa$_6$, Xaa$_7$ and Xaa$_8$ are Lys, His or Arg;

Z is absent or comprises an N-terminal acyl group linked to the N-terminal of the peptide sequence;

with the proviso that Xaa$_5$, Xaa$_6$, Xaa$_7$ and Xaa$_8$ are not aromatic or negatively charged amino acids.

The PACE4 inhibitor described herein can comprise a peptide sequence having amino acids that can be any non-natural amino acids, such as for example 2-aminoadipic acid, 3-aminoadipic acid, alanine, 3-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-di-aminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine or ornithine.

In another aspect, it is provided a PACE4 inhibitor consisting of a peptide sequence consisting of the following formula:

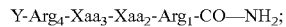

wherein

Arg$_1$ is an arginine, arginine derivative, arginine mimetic or a transition state analogue;

Xaa$_2$ and Xaa$_3$ are any amino acids or stereoisomers thereof; and

Y is absent or comprises the formula Z-Xaa$_8$-Xaa$_7$-Xaa$_6$-Xaa$_5$, wherein

Xaa$_5$, Xaa$_6$, Xaa$_7$ and Xaa$_8$ being positively charged amino acids or stereoisomers thereof;

Xaa$_5$, Xaa$_6$, Xaa$_7$ and Xaa$_8$ have an hydrophobicity score between about 4.5 to −0.4 based on a Kyte-Doolittle hydrophobicity plot, or Xaa$_5$, Xaa$_6$, Xaa$_7$ and Xaa$_8$ are Lys, His or Arg;

Z is absent or comprises an N-terminal acyl group linked to the N-terminal of the peptide sequence;

with the proviso that Xaa$_5$, Xaa$_6$, Xaa$_7$ and Xaa$_8$ are not aromatic or negatively charged amino acids.

In another aspect, it is provided a PACE4 inhibitor consists essentially of a peptide sequence consisting of the following formula:

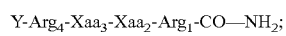

wherein

Arg$_1$ is an arginine, arginine derivative, arginine mimetic or a transition state analogue;

Xaa$_2$ and Xaa$_3$ are any amino acids or stereoisomers thereof; and

Y is absent or comprises the formula Z-Xaa$_8$-Xaa$_7$-Xaa$_6$-Xaa$_5$, wherein

Xaa$_5$, Xaa$_6$, Xaa$_7$ and Xaa$_8$ have an hydrophobicity score between about 4.5 to −0.4 based on a Kyte-Doolittle hydrophobicity plot, or Xaa$_5$, Xaa$_6$, Xaa$_7$ and Xaa$_8$ are Lys, His or Arg;

Z is absent or comprises an N-terminal acyl group linked to the N-terminal of the peptide sequence;

with the proviso that Xaa$_5$, Xaa$_6$, Xaa$_7$ and Xaa$_8$ are not aromatic or negatively charged amino acids.

A Kyte-Doolittle hydrophobicity plot allows for the visualization of hydrophobicity over the length of a peptide sequence. A hydropathy scale which is based on the hydrophobic and hydrophilic properties of the 20 amino acids is used. Hydrophobicity (or hydrophilicity) plots are designed to display the distribution of polar and apolar residues along a protein sequence (Kyte and Doolittle, 1982, J. Mol. Biol., 157: 105).

Xaa$_5$, Xaa$_6$, Xaa$_7$ and Xaa$_8$ can be positively charged amino acids or stereoisomers thereof. Xaa$_5$, Xaa$_6$, Xaa$_7$ and Xaa$_8$ can be Leu, Ile, Val or their analogues.

Xaa$_5$, Xaa$_6$, Xaa$_7$ and Xaa$_8$ are thus not an aromatic amino acid which comprises a side chain which contains an aromatic ring system. Such amino acids are for example Phe, Trp, Tyr and His.

Xaa$_5$, Xaa$_6$, Xaa$_7$ and Xaa$_8$ are thus not a negatively charged amino acids such as Glu and Asp.

In another embodiment, it is disclosed a composition comprising a PACE4 inhibitor as defined herein and a carrier.

In accordance with the present invention, a carrier or "pharmaceutical carrier" is a pharmaceutically acceptable solvent, suspending agent or any other pharmacologically inert vehicle for delivering one or more active compounds to an animal, and is typically liquid or solid. A pharmaceutical carrier is generally selected to provide for the desired bulk, consistency, etc., when combined with components of a given pharmaceutical composition, in view of the intended administration mode. Typical pharmaceutical carriers include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycotate, etc.); and wetting agents (e.g., sodium lauryl sulphate, etc.).

Figure 5A:
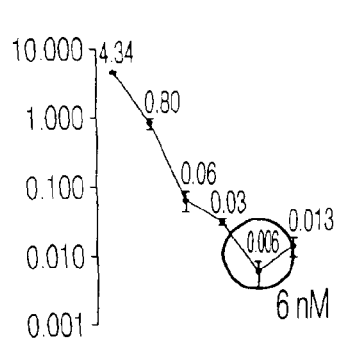
FIGS. 5A-G illustrates the effects of adding from 0- to 6 leucine residues (multileucine or ML) to the N-terminal of the RXKR consensus sequence (with X chosen to be a Val) on the inhibition of (A) PACE4, (B) PC5/6, (C) PC7, (D) Furin, (E) PC2, (F) PC1/3 and (G) PC4.
Figure 5B:
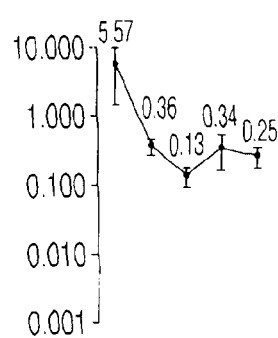
Figure 5C:
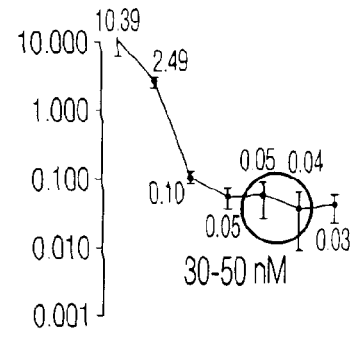
Figure 5D:
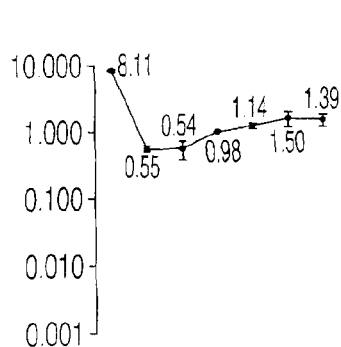
Figure 5E:
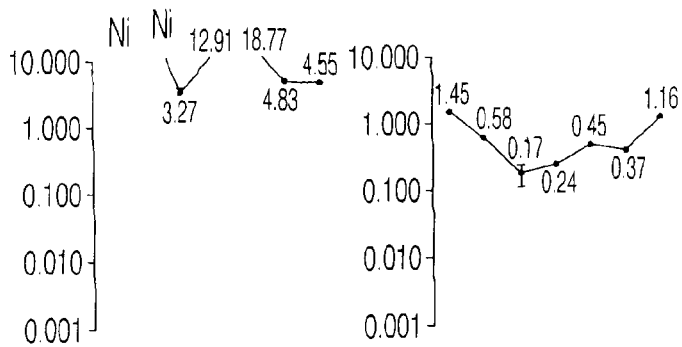
Figure 5F:
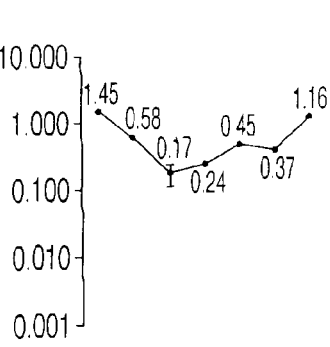
Figure 5G:
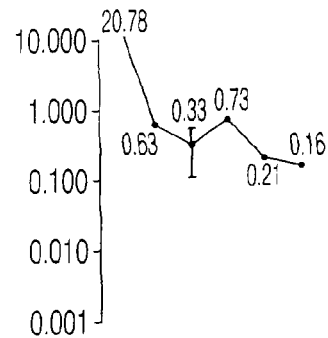
Figure 6:
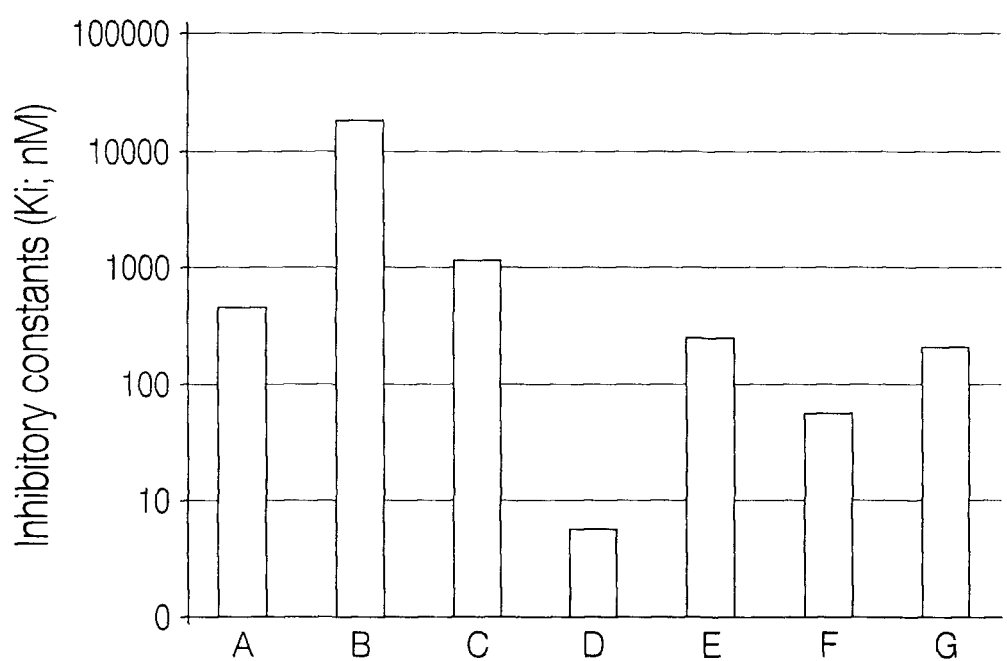
FIG. 6 illustrates the inhibition of the LLLLRVKR (SEQ ID NO: 5) peptide on (A) PC1/3 (454 nM), (B) PC2 (18769 nM), (C) Furin (114 nM), (D) PACE4 (5.5 nM), (E) PC5/6 (245 nM), (F) PC7 (54 nM) and (G) PC4 (205 nM) as plotted as an histogram wherein the y axis is a log scale of the inhibitory constants measured in nM.

A series of PC peptide inhibitors with varying degrees of selectivity and potency were tested for various PCs (see FIGS. 5 and 6). One compound stand out: LLLLRVKR—NH$_2$ (four leucine or multi-leu peptide; SEQ ID NO: 5) was the most potent inhibitor of PACE4 (K$_i$ of 6 nM) evaluated in this study and was significantly more effective on PACE4 than the other PCs (9-folds and more; see FIG. 5A as encircled and FIG. 6). Thus, LLLLRVKR—NH$_2$ (SEQ ID NO: 5) is a selective inhibitor of PACE4 (Ki=5 nM), with next best inhibition against PC7 (K$_i$=50 nM). An inhibitor having an affinity or selectivity in the nM range represents an indication of the potential efficacy of the inhibitor in vivo.

According to another aspect, it is disclosed a method of screening for a PACE4 inhibitor comprising the steps of contacting an agent with a PACE4 protein. Alternatively, a fragment of PACE4, wherein for example the Cys rich region has been removed, and has an activity similar to the wild-type PACE4 can also be used in the screening method (see ref Mains et al., 1997, Biochem J., 321: 587-593).

The agent can be firstly identified by techniques commonly used in the art. As an example, but not restricted to, positional scanning synthetic peptide combinatorial libraries (PS-SPCL) and the incremental peptide assay (IPA) techniques can be used. Assessing the activity of the PACE4 protein can be accomplished by techniques known in the art.

Those skilled in the art can easily determine PACE4 activity using routine experimentation. For example, the activity assay of PACE4 can be carried out in 96 well plates, and includes the use of a fluorogenic substrate, namely PyrRTKR-AMC (SEQ ID NO: 30) (AMC is amino-methyl-coumarin). The substrate and the purified enzyme are placed in the wells, and depending on the units of enzyme present, the AMC moiety will be cleaved at a certain rate, such a pmoles/sec. The resultant free AMC is now fluorescent and can be detected with a spectrofluorometer. The addition of inhibitors to the assay will yield progress curves that have lesser slopes. Based on these changes the inhibitory constants (K$_i$) is calculated (Fugere et al., 2002, J. Biol. Chem., 277:7648-56).

Reduction of the activity of the PACE4 protein contacted by the agent compared to the basal activity of the PACE4 protein without the agent is indicative that the agent is an inhibitor of PACE4. Basal enzyme activity in a cell is generally defined by the amount of protein or RNA present in a cell, assuming that more enzyme, protein or mRNA means more enzyme activity. Thus, for example but not restricted to, the basal activity of PACE4 can be evaluated by RNA measurements, such as quantitative PCR or Northern blot analysis, or by protein measurements such as Western blots.

In alternate embodiment, it is described a method of identifying a cell proliferation inhibitor, comprising the steps of contacting an agent with a PACE4 protein in the cell and assessing the activity of the PACE4 protein, wherein reduction of the activity of the PACE4 protein contacted by the agent compared to the basal activity of the PACE4 protein without the agent is indicative that the agent is an inhibitor of PACE4 inhibiting cell proliferation. The proliferation rate of the cell can be compared to a control cell not contacted with the agent.

Further optimization of these inhibitors is described herein in cell-based assays or in vivo. N-terminal acylation and C-terminal amidation are valuable modifications to protect against amino- and carboxy-peptidases, respectively.

Other encompassed structural modifications are those enhancing cell permeability, since PACE4 is an intracellular target. In an embodiment, N-terminus acylation can be with fatty omega amino acids or with steroid derivatives. In another embodiment, the fatty omega acids can be selected from the group consisting of 11-amino undecanoyl and 8-amino octanoyl, but not restricted to. The steroid derivatives can be, for example, cholyl.

Other known modifications are, but not restricted to: acyls other then acetyl group, alkyl groups including octyl and undecanyl, alkens and poly alkens saccharides (such as sugars, oligo and polysugars, as well as aminosugars, glucosamine and N-acetyl glucosamine), isoprenoids (e.g. farnesyl and geranyl), fatty amino acids, polyethylene glycols (PEGs), TAT peptide or peptide-like sequences for cell mediated delivery.

Figure 7A:
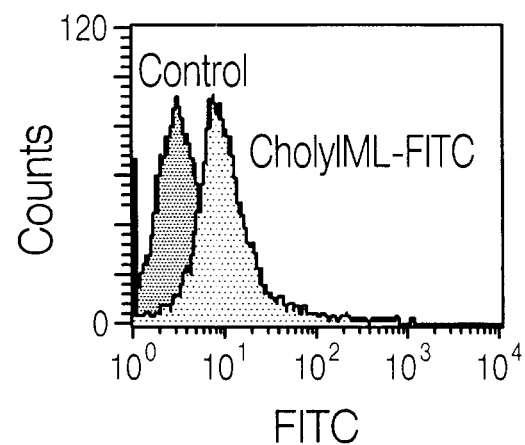
FIG. 7 illustrates flow cytometry results of the ability of the ML peptide to penetrate into DU145 cells wherein cells were treated with the cholyl-ML peptide linked to FITC demonstrating that there is a clear shift of the cells indicating that the cholyl-ML FITC peptide has penetrated the cells with (A) or without (B) being treated with trypsin to insure that the observed shift was not due to the cholyl-ML FITC peptide unabsorbed on the cell surface.
Figure 7B:
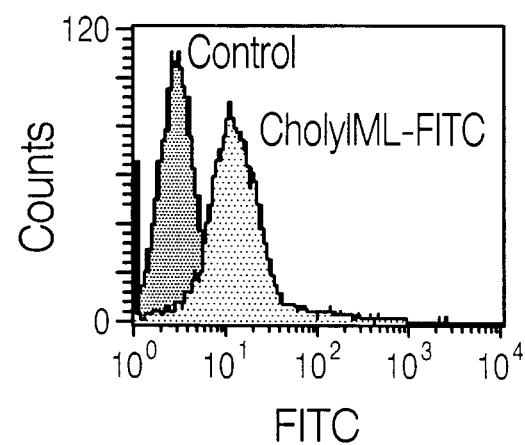

Modifications to examine the cell penetration of inhibitors were carried out by adding of a fluorescent marker (such as FITC) to the N-terminus of the peptides (FIG. 7). These modifications can be tested in cell culture assays combined with flow cytometry analysis, to examine cell penetration. Cells were treated with the cholyl-ML peptide linked to FITC (see Table 2). Following treatment, there is a clear shift of the cells indicating that the cholyl-ML FITC peptide has penetrated the cells (FIG. 7A). As a further control, cells were treated with trypsin (FIG. 7B) to insure that the observed shift was not due to the cholyl-ML FITC peptide absorbed on the cell surface. It is demonstrated herein that substantial cell penetration of the peptide is most likely due to its very hydrophobic multi-leucine structure. In an alternate embodiment, cell penetration can be increased by the addition of fatty moieties to the peptidic sequences, such as cholesterol derivatives (cholic acid) or fatty amino acids (6-amino-caproic acid, 8-amino caprylic acid, 11-amino-dodecanoic acid).

The effects of the PACE4 inhibitors on cell proliferation were evaluated. MTT assay was used to evaluate the effects of PACE4 inhibitors on cell proliferation. MTT (3-(4,5-Dimethylthiazol-2-yl)-2,5-diphenyltetrazolium bromide) assay is a standard colorimetric assay for measuring cellular proliferation. Yellow MTT is reduced to purple formazan in the mitochondria of living cells. This reduction takes place only when mitochondrial reductase enzymes are active. Conversion is directly related to the number of viable cells. The MTT assay is quantitative and more sensitive than viability using trypan blue and can also be adapted to 96 well formats, whereas trypan blue tests must be read individually. Because the MTT assay requires less cell manipulation than [$^3$H]thymidine incorporation assays (no cell harvesting or medium changes are necessary), the possibility of error is reduced and the standard deviation values are lower. Comparisons between [$^3$H]thymidine incorporation and MTT assays have demonstrated less than 5% difference for determination of growth factor response. Other assays also known can be used to determine the effects of an inhibitor on the proliferation of a cell.

Figure 8:
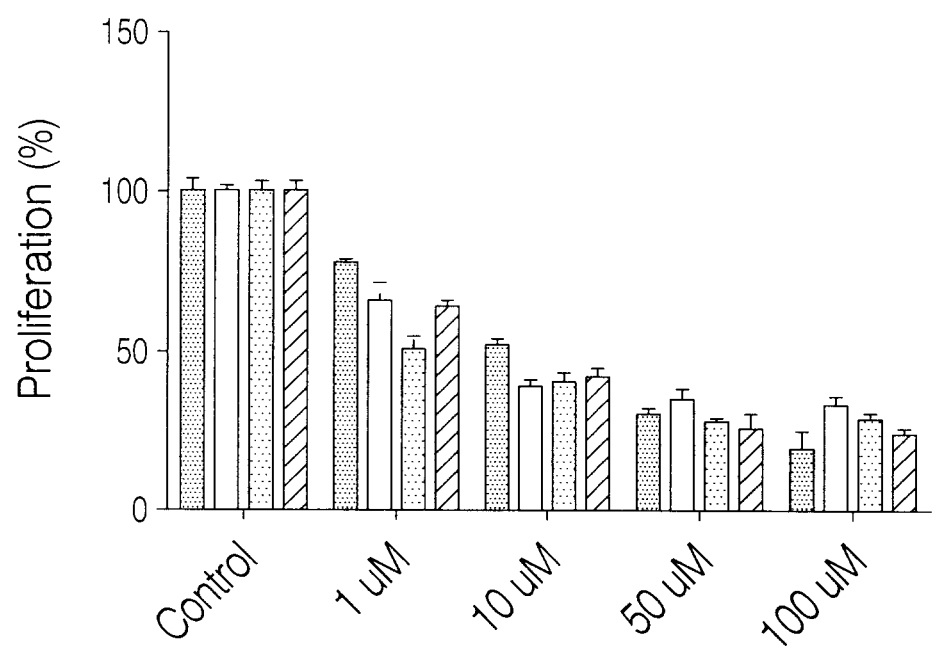
FIG. 8 illustrates the proliferation index in function of the concentration of acetyl-ML peptide added for various cell types. For comparison, a vehicle treatment (control) was also administered. Small cell carcinoma cell line H345 (white histogram), gliobastoma U251 cell line (black histogram), prostatic cell line DU145 (shaded histogram) and sarcofibroma HT1080 cell line (gray histogram) were all treated with increasing amounts of the acetyl-ML peptide.

Various cell lines were tested, namely HT1060 (human fibrosarcoma), H345 (human SCLC-small cell lung carcinoma), U251 (human glioma) and DU145 cell lines (human prostatic cancer). PACE4 mRNA was expressed in each cell line. In all cases, both ML and acetyl-ML peptides had significant effects on the cell proliferation index (FIG. 8). Inhibitors can be used in any cell line expressing PACE4.

Figure 9:
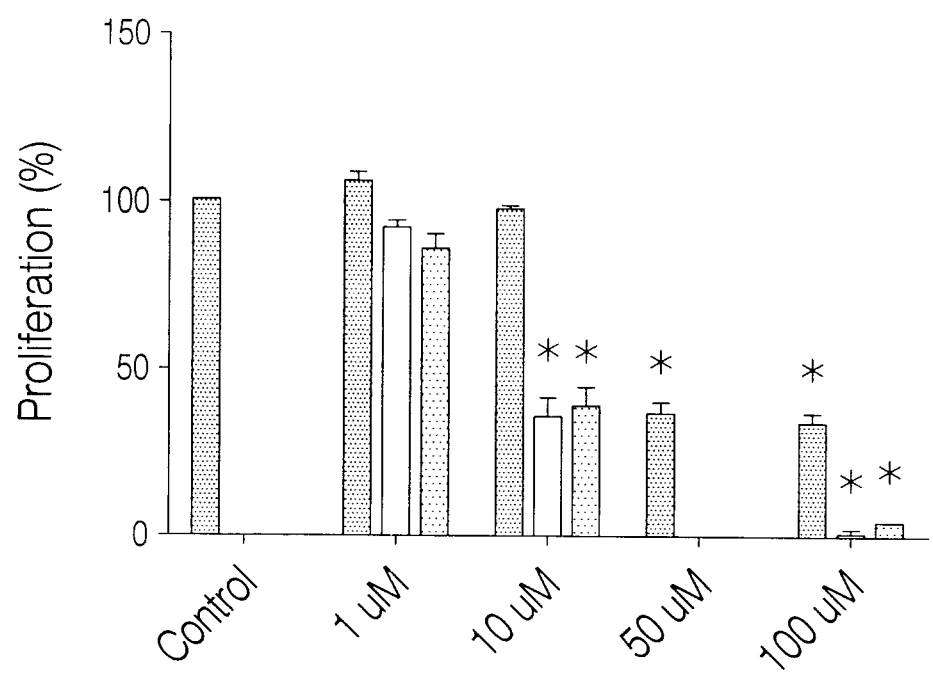
FIG. 9 illustrates the proliferation index in function of the concentration of peptide added for DU145 cells. For comparison, a vehicule treatment (control) was also administered. 8-amino octanoyl-ML peptide (black histogram), 11-amino undecanoyl-ML peptide (white histogram) or cholyl-ML peptide (gray histogram) were all administered to DU145 cells. The (*) indicates that values are mean±SEM; *$P<0.05$.

ML and acetyl-ML peptides with lipid or sterol N-terminal peptides were also compared with the prostatic cell line DU145. 8-amino octanoyl-ML ($H_2N-CH_2-(CH_2)_6-CO-NH$-LLLLRVKR-$CONH_2$) (SEQ ID NO: 31); or C8: $CH_3-(CH_2)_6-CO-NH$-LLLLRVKR-$CONH_2$) (SEQ ID NO: 5), 11-amino undecanoyl-ML ($H_2N-CH_2-(CH_2)_9-CO-NH$-LLLLRVKR-$CONH_2$ (SEQ ID NO: 32); or C11: $CH_3-(CH_2)_9-CO-NH$-LLLLRVKR-$CONH_2$) (SEQ ID NO: 5) or cholyl-ML (cholyl-NH-LLLLRVKR-$NH_2$) (SEQ ID NO: 5) peptides all had more potent effects than ML or acetyl-ML peptides, most likely due to their additional ability to penetrate the cell membranes (FIG. 9).

Accordingly, it is disclosed herein a method of lowering PACE4 activity in a cell, comprising contacting a PACE4 inhibitor as defined herein or with the cell, thereby lowering PACE4 activity in the cell. Preferably, the activity of PACE4 needs to be lowered by less than 50%, more preferably less than 40%, less than 30%, or less than 25%. Alternatively, the activity of PACE4 is lowered sufficiently to inhibit the activity of growth factors.

In another embodiment a method of reducing proliferation of a cell in a subject, comprising administering a PACE4 inhibitor to the subject is also encompassed.

Figure 10A:
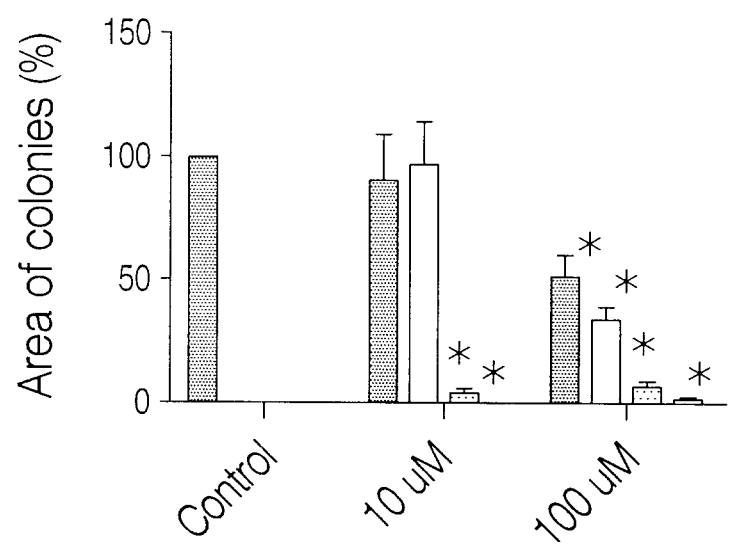
FIG. 10 illustrates (A) areas covered by colonies as a % of DU145 cell lines treated with a vehicle (control), 10 or 100 μM of acetyl-ML (black histogram), 8-amino octanoyl-ML (white histogram), 11-amino undecanoyl-ML (gray histogram) and cholyl-ML (shaded histogram). Photographic representations of a dish showing colonies of DU145 cells (B) treated with the vehicle or (C) 100 μl of 8-amino octanoyl-ML is illustrated. The (*) indicates that values are mean±SEM (n=2 to 4); *$P<0.05$.
Figures 10B, 10C:
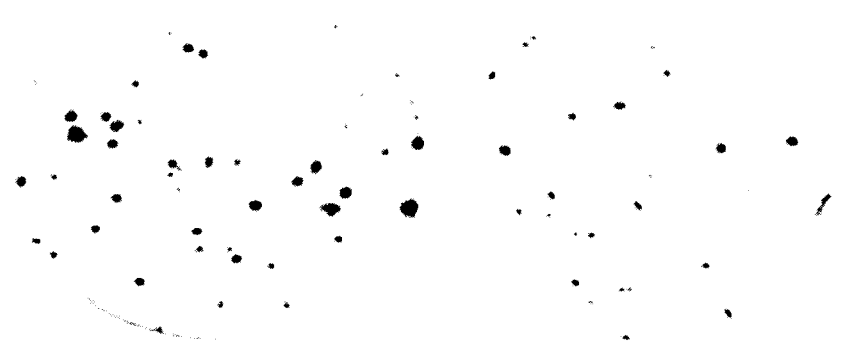

A clonogenic assay was used to study the effectiveness of the inhibitors described herein on the colony forming potential of DU145 cells. The clonogenic assay or colony formation assay is a survival assay based on the ability of a single cell to grow into a colony. The assay essentially tests every cell in the population for its ability to undergo "unlimited" division. All ML peptides tested had important effects on the ability of DU145 cell lines to form colonies. The most potent effects were observed with lipid or sterol ML peptides (or octanoyl-ML, FIG. 10A). Other techniques to study the effectiveness of the inhibitors described herein include, but are not limited to, annexin assay, soft agar assay, Boyden chambers or crystal violet assay. Assays that measure the levels of caspase can also be useful to evaluate apoptosis.

The present invention further concerns the use of RNA interference (RNAi) to modulate PACE4 expression in target cells. "RNA interference" refers to the process of sequence specific suppression of gene expression mediated by small interfering RNA (siRNA) without generalized suppression of protein synthesis. While the invention is not limited to a particular mode of action, RNAi may involve degradation of messenger RNA (e.g., PACE4 mRNA) by an RNA induced silencing complex (RISC), preventing translation of the transcribed targeted mRNA. Alternatively, it may involve methylation of genomic DNA, which shuts down transcription of a targeted gene. The suppression of gene expression caused by RNAi may be transient or it may be more stable, even permanent.

"Small interfering RNA" of the present invention refers to any nucleic acid molecule capable of mediating RNA interference "RNAi" or gene silencing. For example, siRNA of the present invention are double stranded RNA molecules from about ten to about 30 nucleotides long that are named for their ability to specifically interfere with protein expression. In one embodiment, siRNA of the present invention are 12-28 nucleotides long, more preferably 15-25 nucleotides long, even more preferably 19-23 nucleotides long and most preferably 21-23 nucleotides long. Therefore preferred siRNA of the present invention are 12, 13, 14, 15, 16, 17, 18, 19, 20, 21, 22, 23, 24, 25, 26, 27, 28 nucleotides in length. As used herein, siRNA molecules need not to be limited to those molecules containing only RNA, but further encompass chemically modified nucleotides and non-nucleotides.

siRNA of the present invention are designed to decrease PACE4 expression in a target cell by RNA interference. siRNA of the present invention comprise a sense region and an antisense region wherein the antisense region comprises a sequence complementary to a PACE4 mRNA sequence and the sense region comprises a sequence complementary to the antisense sequence of PACE4 mRNA. A siRNA molecule can be assembled from two nucleic acid fragments wherein one fragment comprises the sense region and the second fragment comprises the antisense region of siRNA molecule. The sense region and antisense region can also be covalently connected via a linker molecule. The linker molecule can be a polynucleotide linker or a non-polynucleotide linker.

The binding free energy for a nucleic acid molecule with its complementary sequence is sufficient to allow the relevant function of the nucleic acid to proceed (e.g., RNAi activity). For example, the degree of complementarity between the sense and antisense region (or strand) of the siRNA construct can be the same or can be different from the degree of complementarity between the antisense region of the siRNA and the target RNA sequence (e.g., PACE4 RNA sequence). Complementarity to the target sequence of less than 100% in the antisense strand of the siRNA duplex (including deletions, insertions and point mutations) is tolerated when these differences are located between the 5'-end and the middle of the antisense siRNA. Determination of binding free energies for nucleic acid molecules is well known in the art. Examples of functional siRNA against PACE4 are disclosed in Table 1.

TABLE 1

| siRNA probes against PACE4 | |
|---|---|
| siRNA name | Sequence |
| TRCN0000075243 | CCGGGAGAGAAGTCTCCTCTGCATTCTCGAGA ATGCAGAGGAGACTTCTCTCTTTTTG (SEQ ID NO: 25) Clone ID: NM_017573.2-1238s1c1 Accession Number(s): NM_017573.3 Region: 3UTR |
| TRCN0000075244 | CCGGCCTAGAGAACAAGGGCTACTACTCGAGTA GTAGCCCTTGTTCTCTAGGTTTTTG (SEQ ID NO: 26) Clone ID: NM_017573.2-469s1c1 Accession Number(s): NM_017573.3 Region: CDS |
| TRCN0000075245 | CCGGAGGCTACAACAACTGGGTCTTCTCGAGAA GACCCAGTTGTTGTAGCCTTTTTG (SEQ ID NO: 27) Clone ID: NM_017573.2-397s1c1 Accession Number(s): NM_017573.3 Region: CDS |
| TRCN0000075246 | CCGGCCTCCCACTATACGCCTGGCTCTCGAGAG CCAGGCGTATAGTGGGAGGTTTTTG (SEQ ID NO: 28) Clone ID: NM_017573.2-994s1c1 Accession Number(s): NM_017573.3 Region: CDS |

TABLE 1-continued siRNA probes against PACE4

| siRNA name | Sequence |
|---|---|
| TRCN0000075247 | CCGGCCCTTGGACGTCAGCACTGAACTCGAGTT<br>CAGTGCTGACGTCCAAGGGTTTTG<br>(SEQ ID NO: 29)<br>Clone ID: NM_017573.2-377s1c1<br>Accession Number(s): NM_017573.3<br>Region: CDS |

Figure 11A:
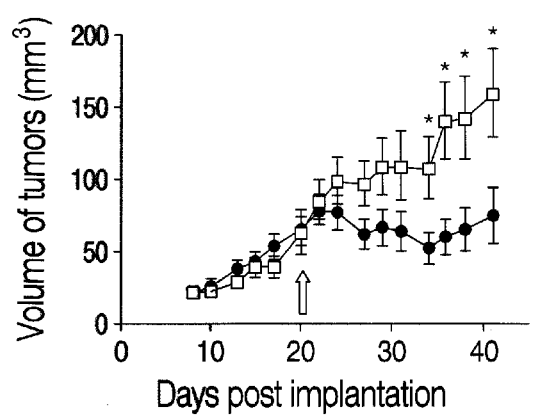
FIG. 11 illustrates (A) the in vivo volume of tumors inhibition by a vehicle (grey) or choly-ML peptide (black) of DU145 cells implanted sc at two sites on the backs of Nu/Nu mice, which lack an immune system. Representative control (1) and treated mice (2) are shown on the (B) panel, while panels (C) and (D) show the histology of the control (C) and treated tumors (D). The (*) indicates that values are mean±SEM (n=5).
Figure 11B:
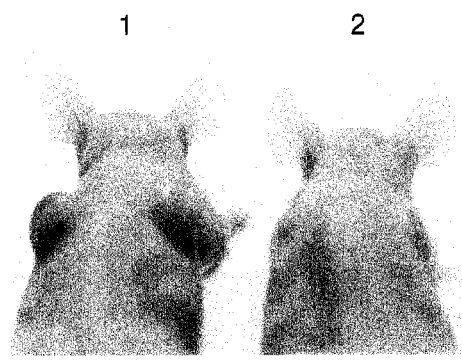
Figure 11C:
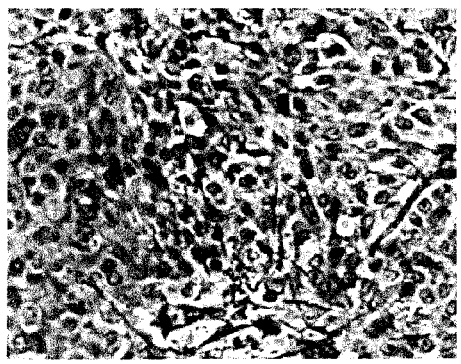
Figure 11D:
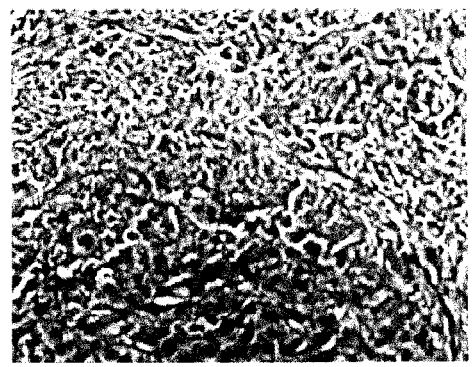
Figure 12A:
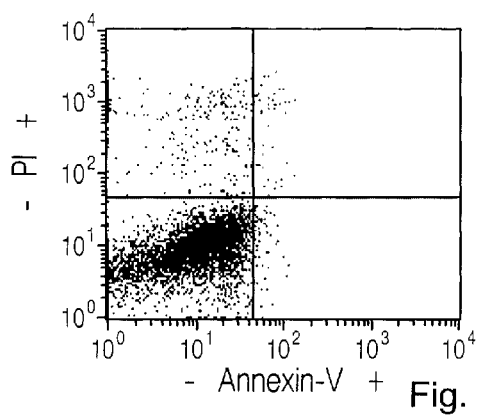
FIG. 12 illustrates flow cytometry results showing the apoptosis induction using annexin-V-FITC/propidium iodide staining wherein dot plots show the presence of extracellular phosphatidylserine and the permeability for propidium iodide (PI) of DU145 (A and B) and 4-2 cells (C and D) untreated (A and C) or incubated (B and D) for 48 h with 66 μM cisplatin, and wherein for each plot, the horizontal lines separate annexin-V positive from negative cells; the vertical lines separate PI-positive and –negative cells.
Figure 12B:
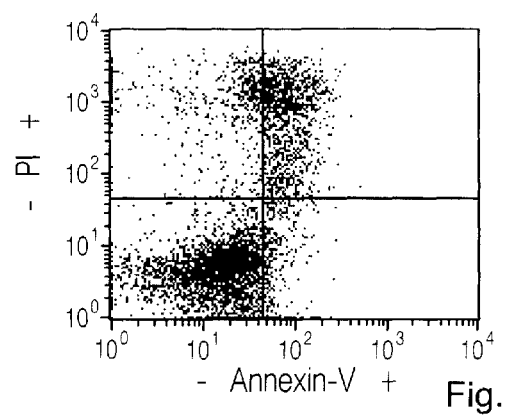
Figure 12C:
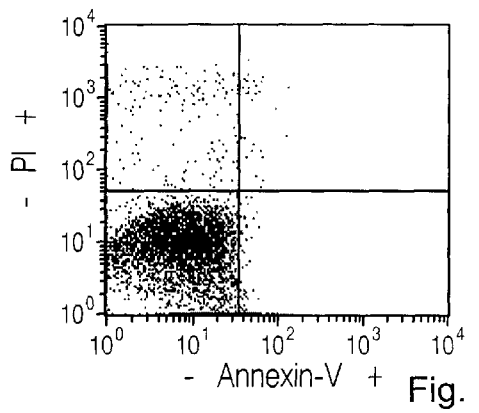
Figure 12D:
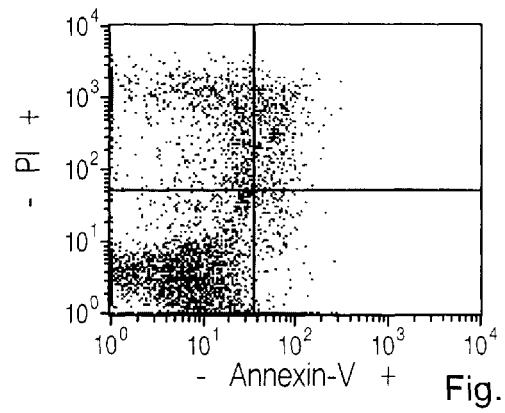

To test the effects of PACE4 inhibitors in vivo, a nude mouse model was used in order to validate PACE4's role in tumor progression within an integrated system. A nude mouse is a genetic mutant that lacks a thymus gland, resulting in an inhibited immune system due to a greatly reduced number of T cells. The genetic basis of the nude mouse mutation is a disruption of the Foxn1 gene. The nude mouse can receive many different types of tissue and tumor grafts, as it mounts no rejection response. These xenografts are commonly used to test new methods of treating tumors. Nude mice were used to test the tumor progression of control DU145 cells compared to PACE4 silenced DU145 cells (clone 4-2) (FIG. 11). Control tumor received vehicle (DMSO) injections. Control tumor continued their growth pattern, reaching an average size of 160 mm$^3$, while treated tumors only reached a size of 75 mm$^3$ (FIG. 11A). Consequently, PACE4 inhibition by the specific inhibitors described herein reduces tumors growth. The nude mouse model is well known and extensively tested (Naomoto et al., 1987, J. Cancer Res. Clin. Oncol., 113: 544-549; Taetle et al., 1987 Cancer Treat. Rep. 71: 297-304).

Accordingly to another embodiment, it is disclosed a method of reducing tumor growth in a subject, comprising administering a PACE4 inhibitor as described herein to a subject. In a further embodiment, it is disclosed a method for the prophylaxis or treatment of a cancer in a subject, comprising administering to a subject in need of such treatment a therapeutically effective amount of a PACE4 inhibitor as defined herein. Preferably, the tumors are completely blocked from growing in vivo. More preferably, tumors are completely blocked from growing by 75%, more preferably 66%, alternatively by 50%.

The method described herein can be used to treat prostate cancer. In addition, other model cell lines have also been reduced in their proliferative index when treated with ML peptides. For example, SCLC cell line H345 (a small cell lung carcinoma), HT1080 cells (a fibrosarcoma), or in U251 (a glioblastoma) have also been tested. The ML peptides reduced their proliferation.

Tests were also conducted in order to determine if reductions in cell proliferation was due to cell death occurring by apoptosis. The annexin V assay is based on the observation that soon after initiating apoptosis, cells translocate the membrane phosphatidylserine from the inner face of the plasma membrane to the cell surface. Once on the cell surface, phosphatidylserine can be easily detected by staining with a fluorescent conjugate of Annexin V, a protein that has a high affinity for phosphatidylserine. Detection is analyzed by flow cytometry. On DU145 cells at various concentrations (1-100 μM), no changes on live, early apoptotic or late apoptotic/necrotic cells populations was seen (FIG. 12). This data re-enforces the notion that PACE4 inhibitors have effects through reductions of proliferation pathways and not through effects on apoptotic pathways. Other methods that can be used to measure apoptosis includes, but not limited to, the annexin assay, measurement of caspases, DNA fragmentation assays, TUNEL assay or detection of apoptosis related molecules such as FAS or p53.

The present invention will be more readily understood by referring to the following examples which are given to illustrate the invention rather than to limit its scope.

EXAMPLE 1

PACE4 Expression in Clinically Localized Prostate Tumors

Forty-seven primary prostate tumors samples obtained from patients undergoing surgery were tested for PACE4 expression. Prostate tumor samples were obtained from patients either at St-Louis and Bichat Hospital (Paris, France), or Tournan's clinic (Tournan en Brie, France). Samples tissues from the thirty-four patients with clinically localized prostate tumors were obtained by removing clinically localized tumors by radical prostatectomy. The surgical specimens were first sliced thickly, and samples were then cut from suspect areas. Part of the selected tissue was immediately placed in liquid nitrogen for RNA extraction, while adjacent sections were stained with H/E (hematoxylin and eosin) for histopathological examination. The sample tissues from hormone-refractory recurrent prostate carcinoma were obtained from patients with metastatic disease at diagnosis. Since these patients were not amenable to radical surgery, they received endocrine therapy, either by classical androgen deprivation (orchidectomy or luteinizing-hormone-releasing hormone (LHRH) agonist administration); or, by maximal androgen blockade (castration combined with antiandrogen therapy). These patients relapsed, and their tumors became clinically androgen-independent.

Only tissues where all epithelial cells were neoplastic were dissected and used. Suspect areas were examined histopathologically in the surgery suite, and a thick shave section was taken for research purposes. This pre-selected tumor specimen section was then sliced on each side in the laboratory and again subjected to pathological examination. Samples were considered suitable for molecular studies when all epithelial cells were neoplastic. Confirmed malignant areas were carefully dissected using a scalpel. This process yields a homogeneous cell population and thereby avoids dilution of tumor-specific genetic changes by nucleic acids from normal and reactive cells present in the same specimen. The tissues were grouped into similar clinical stages based on TNM system as: eighteen pT2 samples (tumors strictly confined to the organ), sixteen pT3 samples (tumors with extracapsular extension), and thirteen hormone-refractory samples (tumors no longer responsive to endocrine therapy).

Nine well-characterized matched normal prostate specimens from the thirty-four patients with clinically localized prostate who underwent radical prostatectomy were used to assess basal target-gene mRNA expression. Normal-looking areas of each surgical specimen were examined histologically for the absence of cancer cells and selected upon its microscopic pathological criteria to avoid including areas with benign hyperplasia.

A real-time PCR strategy was used to evaluate PACE4 mRNA expression levels in prostate tumor tissues using the nine matched normal prostate tissues as a reference (FIG. 1A). Total RNA was extracted from tissue specimens by using the acid-phenol guanidium method. The quality of RNA samples was determined by electrophoresis through agarose gels, staining with ethidium bromide, and visualization of the 18S and 28S RNA bands under ultraviolet light. RNA was reverse-transcribed.

All PCR reactions were performed using an ABI Prism 7900HT Sequence Detection System (Applied Biosystems) and the SYBR® Green PCR Core Reagents kit (Perkin-Elmer Applied Biosystems). Briefly, the thermal cycling conditions comprised an initial denaturation step at 95° C. for 10 min and 45 cycles at 95° C. for 15 s and 65° C. for 1 min. A genomic DNA and non-template control was included in each experiment. Samples and controls were tested in duplicate. Primers were chosen with the assistance of the computer programs Oligo 4.0 (National Biosciences, Plymouth, Minn.) and Primer Express (Perkin-Elmer Applied Biosystems). Primer sequences for endogenous control genes PPIA (the peptidyl prolyl isomerase A gene encoding cyclophilin A) were described earlier (Chene et al., 2004, Int. J. Cancer, 111: 798-804). The PACE4 primer sequences are: sense, 5'-CAA-GAGACCCAGGAGCATCCC-3' (SEQ ID NO: 8) and, antisense, 5'-ACCCGCTGGTCCGAGTGCT-3' (SEQ ID NO: 9). The threshold cycle (Ct) numbers obtained from PCR amplification were expressed as N-fold differences in target gene expression relative to PPIA expression and termed "Ntarget" values.

The mean relative PACE4 mRNA expression levels (FIG. 1A) were significantly higher in both pT2 and pT3 groups (3.894±0.4933 and 4.211±0.5403, respectively), when compared to the mean level found in normal prostate tissues (2.243±0.2613). However, the mean PACE4 expression level measured in hormone refractory tissues (2.79±0.4359) was not significantly higher than the one measured in controls. Real-time PCR for the other PCs showed that furin, PACE4 and PC7 were the most expressed PCs in normal prostate tissues. However, only PACE4 mRNA levels increased in tumor tissues, while the others showed little variation.

Figure 1B:
Figure 1C:
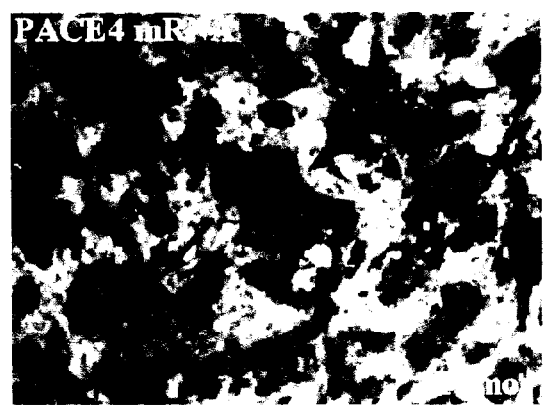

This higher PACE4 expression, particularly in epithelial cells, was directly assessed by an in situ hydridization using digoxigenin-labeled cRNA prodes. Normal prostate tissues showed the expected epithelial cell distribution of PACE4 mRNA. However, tumor tissue showed a disorganization level of tissue structure, with a higher PACE4 expression and even cells invading the stroma (FIG. 1C) compared to normal prostate tissue (FIG. 1B). The in situ was done using a cRNA probe labelled with digoxigenin, as previously described (Dong et al., 1997, J. Neurosci. 17: 563-575).

EXAMPLE 2

Down Regulation of PACE4 mRNA in DU145 Cells by Specific SOFA-δRz

An expression vector containing the tRNA$^{Val}$ promoter to express the PACE4-SOFA-δRz into transfected cells was used. This promoter allows the transcription of a chimeric catalytic RNA containing a tRNAVal motif, which drives the newly synthesized molecule into the cytoplasm of the cells, and the PACE4-SOFA-δRz, that catalyzes the cleavage of the targeted mRNA.

The expression vector ptRNA$^{Val}$/hygromycin, containing the RNA polymerase III promoter tRNAVal promoter for cellular applications was used (see D'Anjou et al., 2004, J. Biol. Chem., 279: 14232-14239). A PCR strategy was used to create a DNA template containing a 5'-KpnI restriction site and a 3'-blunt end. The sequences of the two complementary and overlapping DNA oligodeoxynucleotides (ODNs) used were: sense, 5'-ATCCATCGGGTACCGGGCCAGCTAGT-TT(GGCCTCTGCTAC)$_{BS}$ ($\overline{CA\text{-}AC}$)$_{BL}$ CAGGGTCCACC-3' (SEQ ID NO: 10) and, antisense, 5'-CCAGCTA-GAAAGGGTCCCTT-AGCCATCCGCGAACGGATGCC-CA(ATCAAC)$_{P1}$ ACCGCGAGGAGGTGGACCCTG(GTT-G)$_{BL\text{-}3}$ (SEQ ID NO: 11). The underlined nucleotides (nt) correspond to the KpnI restriction site, and those in parenthesis to the PACE4 specific biosensor (BS), blocker (BL) and P1 stem (P1) of the PACE4-SOFA-δRz. The purified and KpnI-digested PCR product was cloned in the expression vector previously digested with KpnI and EcoRV restriction enzyme. The vector used to restore PACE4 mRNA levels contained the full length PACE4 cDNA and a neomycin resistance gene.

Radiolabeled PACE4 RNA was obtained from transcription of a XhoI-digested pcDNA3 vector containing a chimeric cDNA composed of the PC5/6A signal peptide linked to propACE4 coding sequence using T7 RNA polymerase with 50 µCi of [α-$^{32}$P]GTP. The catalytic RNAs were synthesized using a PCR-based strategy with the expression vectors to generate DNA templates containing a 5'-T7 RNA polymerase promoter. The sense primer 5'-TTAATACGACTCACTATA-CAAAAACCAACTTTGGTACC-3' (SEQ ID NO: 12) or 5'-TTAATACGACTCACTATAGGGCCAGCTAGTTT-3' (SEQ ID NO: 13), complementary to either the tRNA$^{Val}$ promoter or the PACE4-SOFA-δRz, were use. The underlined nucleotides correspond to the T7 RNA polymerase promoter sequence. The antisense ODN sequence used for both PCR was 5'-CCAGCTAGAAAGGGTCCCTTA-3' (SEQ ID NO: 14). After PCR, the purified products were used as templates for T7 RNA polymerase transcription of tRNAVal-PACE4-SOFA-δRz or PACE4-SOFA-δRz. All products were purified on either denaturing 5% or 7.5% PAGE, for PACE4 or PACE4-SOFA-δRz transcripts, respectively.

One of the major advantages of δRz technology is the reduced number of "off-target effects" which sometimes hinders the interpretation of data obtained with siRNA technology. However, even a simple δRz (see D'Anjou et al., 2004, J. Biol. Chem., 279: 14232-14239) can result in a certain number of predicted "off-target" effects due to the limited recognition sequence (i.e., 7 nucleotides). Thus, a second-generation δRz was designed with a "specific on/off adapter" (SOFA adapter). This new design allows a stronger effect on in vitro cleavage assays and a higher specificity for the targeted sequence, with no "off targets" effects. Without wishing to be bound to theory, the SOFA δRz used herein was designed against human PACE4 mRNA, which was used in DU145 cells, and provides an important "proof of concept" for the role of PACE4 in tumor progression.

Before transfecting the vector, a cleavage assay was performed. The SOFA-δRz cleavage assays under single turnover conditions ([SOFA-δRz]>[PACE4 RNA]) were done at 37° C. for 3 hours in a 10 µl reaction containing trace amount of radiolabeled PACE4 RNA and 1 µM of SOFA-δRz in reaction buffer containing 50 mM Tris-HCl, pH 7.5, and 10 mM MgCl$_2$. The reactions were stopped by the addition of loading buffer (97% formamide, 1 mM EDTA (pH 8.0), 0.025% xylene cyanol and 0.025% bromophenol blue), electrophoresed on denaturing 5% PAGE gel, and analysed with a PhosphorImager™ (Amersham Biosciences). This molecule had the same cleavage capacity than the PACE4-SOFA-δRz itself by performing an in vitro cleavage assay before transfecting DU145 cells.

PACE4-SOFA-δRz expression vector was transfected into DU145, a highly invasive, androgen-independent prostate epithelial tumor cell line. Human cancer prostate cell lines DU145 were obtained from ATCC. Cells were maintained in Roswell Park Memorial Institute medium (RPMI 1640) supplemented with 5% fetal bovine serum (Wisent Bioproducts). Cells were grown at 37 C in a water-saturated atmosphere in air/$CO_2$ (5%). Cells were transfected using lipofectamine-2000™ (Invitrogen), and were selected for resistance to hygromycin B (Invitrogen) at 125 μg/ml, with 200 μg/ml of neomycin for double-transfected cells. The stable cell line transfected with the SOFA-δRz expression vector was named 4-2, while the 4-2 cell line stably transfected with the PACE4 expression vector was named 4-2+PACE4. Stable cell lines transfected with the ptRNA$^{Val}$-PACE4-SOFA-δRz were established by the selection of clones resistant to hygromycin B.

Northern blot analyses on total RNA extracts were performed for wild-type DU145 (DU145), DU145 transfected with ptRNA$^{Val}$-PACE4-SOFA-δRz (4-2) and, on 4-2 cells co-transfected with PACE4 cDNA expression vector (4-2+PACE4). Total RNA was isolated from DU145 cells using guanidinium isothiocyanate followed by lithium chloride precipitation. RNA migration (5 μg) on denaturing agarose gel, membrane transfer and $^{32}$P-labeled RNA probe transcriptions were performed. Linearized vectors were used as DNA template for complementary RNA probe transcription using either T7 or SP6 RNA polymerase. The 1066-base pair (bp) cDNA for human furin probe was obtained by digestion of the full-length clone with XhoI enzyme. A 456-bp cDNA fragment of PACE4 was cloned in pGEM-T™ easy vector system (Promega) by RT-PCR reaction on DU145 total RNA with specific primers. This vector was subsequently used for probe transcription. For PC7 probe, a 285-bp rat cDNA was used, and for bovine 18S ribosomal RNA probe, a 600-bp cDNA was used. The ImageJ Software™ 1.37v was used for all densitometric analysis.

As seen in FIG. 2A, the PACE4 mRNA levels in the SOFA-δRz transfected cell line are significantly reduced when compared to the untransfected cells. These levels were partially re-established by the overexpression of PACE4 cDNA. A densitometric analysis using 18S ribosomal RNA as loading control was performed to quantify the mRNA levels in those clonal cell lines using wild type DU145 cells as reference (0.31±0.11 and 0.75±0.06 for 4-2 and 4-2+PACE4, respectively; FIG. 2B). The mRNA levels of two others endogenous expressed PCs were also verified to confirm the specificity of the PACE4-SOFA-(Rz cleavage. Levels of furin and PC7 mRNAs (FIGS. 2C and 2D, respectively) remained mostly unchanged in the 4-2 cells, confirming the reduction of PACE4 expression without significantly affecting the expression of other endogenous PCs.

EXAMPLE 3

The Reduction of PACE4 Expression Slows DU145 Proliferation In Vitro

The total cell numbers of the stable cell lines of Example 2 were counted at different times. The cell proliferation was measured by the colorimetric MTT assay (thiazolyl blue tetrazolium bromide; Sigma-Aldrich). Briefly, cells were seeded in 96-well plate (BD Biosciences) in triplicate with 100 (l of a 3.5×104 cells/ml cell suspension in complete growth medium (RPMI 1640 media supplemented with 5% fetal bovine serum). The following day, cells were carefully washed twice with PBS and media were replaced with 100 (l of either RPMI or conditioned growth media. 48 hours later, 20 (l of a MTT solution (5 mg/ml in PBS 1×) was added to each well for 4.5 h at 37° C./5% CO2. The media was then discarded and the cells were solubilized with 100 μl isopropanol/0.04 N HCl solution. The absorbance was measured at a wavelength of 550 nm with a reference at 650 nm in microplate reader (SpectraMax190™; Molecular Devices). Cells were plated at a density of 5.0×104/well in 6-well plates (BD Biosciences) in duplicates. Complete growth medium was changed after 48 hours. After incubation, cells were washed in PBS, trypsinized and counted in after staining in 0.4% (w/v) trypan blue solution (Sigma). Only viable cells were counted in duplicate.

Figure 3A:
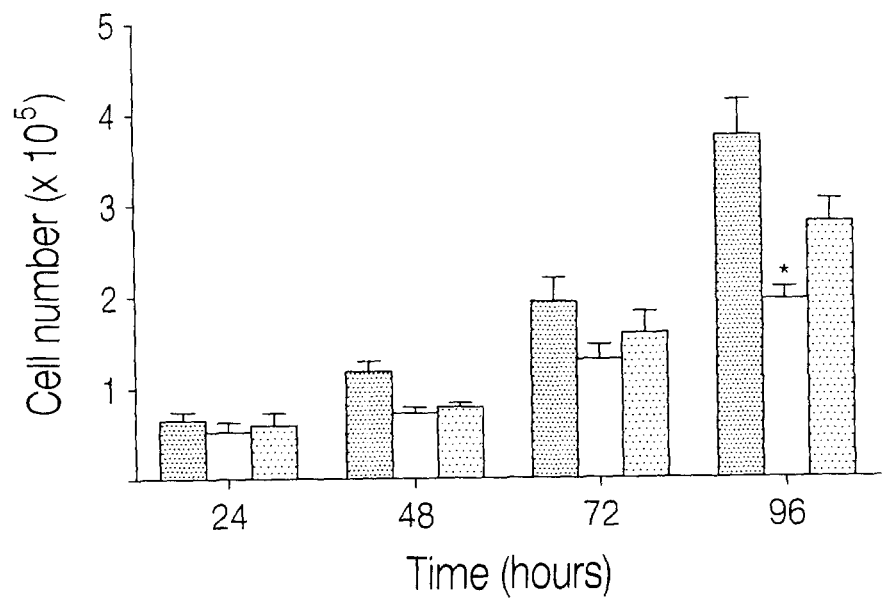
FIG. 3 illustrates that PACE4 knockdown slows DU145 proliferation in vitro since in (A) the total cell number of the stable cell lines showed a significant reduction of proliferation for the 4-2 cells (200,000±14,000 cells; white histogram) when compared to untransfected DU145 (375,000±40,000 cells; black histogram) or 4-2+PACE4 cells (gray histogram), 96 hours after the initial plating. Also shown (B) is an in vitro clonogenic assay on the same cell lines to detect the proportion of cells that retained the capacity to grow into a colony confirming the lower proliferation of DU145 with lowered PACE4 expression (4-2). The (*) indicates that values are mean±SEM (n=9 for DU145 and 4-2+PACE4 and n=7 for 4-2 cells); *$P<0.05$.
Figure 3B:
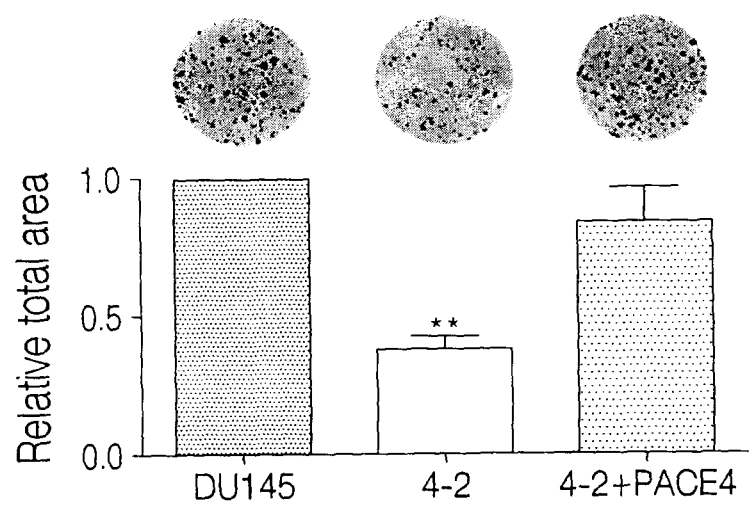

As seen in FIG. 3A, the results showed a significant reduction of proliferation for the 4-2 cells (≈200 000±14 000 cells) when compared to untransfected DU145 (≈375 000±40 000 cells) 96 hours after the initial plating. This reduction was partially reversed in the cell line 4-2+PACE4 (≈280 000±25 000 cells). An in vitro clonogenic assay was also performed on the same cell lines to detect the proportion of cells that retained the capacity to grow into a colony (FIG. 3B). The results of this assay confirmed the lower proliferation of DU145 with lowered PACE4 expression (4-2), as a 68% reduction was observed of cell growth when compared to wild-type DU145. The colony formation capacity of DU145 cells was partially restored (16% less than untransfected cells) in 4-2+PACE4 cells.

EXAMPLE 4

PACE4 Inhibition Prevents Tumor Growth in Xenograft Tumor Model

Figure 4A:
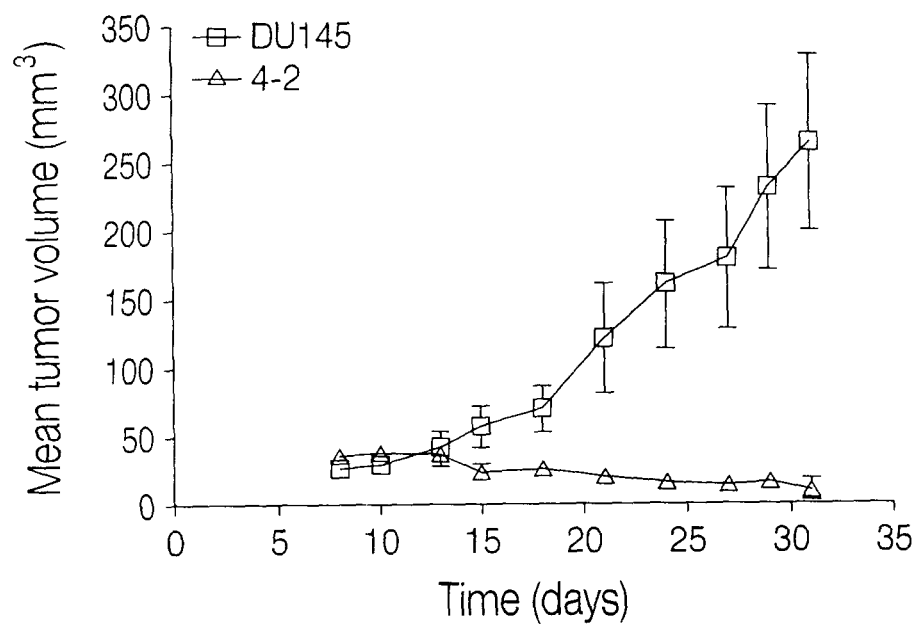
FIG. 4 illustrates in (A) that PACE4 inhibition prevents tumor growth in xenograft tumor model. Results are shown as mean tumor volume ($mm^3$) as the reduction of PACE4 mRNA levels reduced dramatically the ability of 4-2 cells (Δ) to induce tumor growth, while untransfected DU145 cells (□) were able to develop into well-defined tumor masses. Histological analysis in (B) shows the well define tumor mass when DU145 cells (panels A and B) are implanted, which is not seen with the 4-2 cells (panels C and D). Panels B and D of FIG. 4B represent a 400× magnification of panels A and C respectively.
Figure 4B:
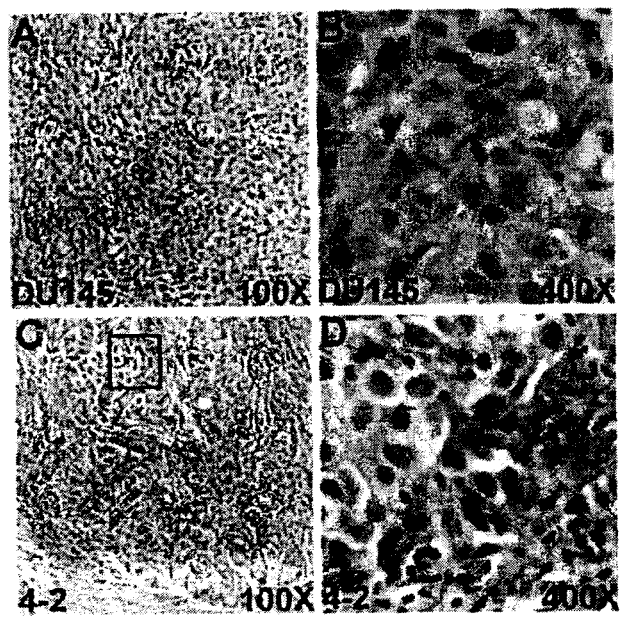

The ability of the experimental cell lines to grow as tumors in mouse model was tested. Four-week-old female athymic nude mice (NU/NU; Charles River Laboratories) were inoculated subcutaneously at the opposite sides of the flank with 3.0×106 cells per inoculums. Cells were grown in complete media and harvested at their exponential growing state. Mice were housed under pathogen free conditions and the implantations were done under anesthesia conditions in laminar flow hood. Xenografts were measured three times per week and volume (V) was determined by this equation: V=(L×W2)×0.5, where L is the length and W is the width of a xenograft. As shown in FIG. 4A, the reduction of PACE4 mRNA levels (see (in FIG. 4A) reduced dramatically the ability of 4-2 cells to induce tumor growth, while untransfected DU145 cells (see (in FIG. 4A) were able to develop into well-defined tumor masses. Histological analysis (FIG. 4B) shows the well define tumor masses when DU145 cells are implanted (see panels A and B in FIG. 4B), however, no such compact and well define structure is obtained with the 4-2 cells (see panels C and D in FIG. 4B), confirming that the lack of PACE4 has significant effects on tumor progression.

EXAMPLE 5

Generation of Potent Inhibitors of PACE4 and PC7

One of the keys to the development of potent and selective PC inhibitors is an understanding of the substrate-binding pocket. The deepest region of the substrate-binding pocket accommodates the consensus motif RXKR ($P_4$-$P_3$-$P_2$-$P_1$) nearly identical in all PCs. Using an incremental peptide assay (IPA), the core warhead sequence, RVKR (SEQ ID NO: 1), was extended one amino acid at a time. In the N-terminal version of this assay, peptides bearing the 20 natural L-amino acids at the $P_5$ position were synthesized and tested. The most efficient inhibitory peptides (pentapeptides) were modified further, by individually adding the 20 L-amino acid at the $P_6$ position, and so forth creating inhibitor peptides with multi-leucines (see Table 2). Thus, the effect of extending the N-terminal side of the core sequence RVKR—$NH_2$ (SEQ ID NO:

1) with multiple leucines on the inhibition potency and specificity of PCs was tested. RVKR—NH$_2$ (SEQ ID NO: 1) was a poor micromolar inhibitor of all PCs, but was most potent on PC1/3 (FIG. 5 and as schematized in FIG. 6).

TABLE 2

Designed peptides/PACE4 inhibitors

| Peptides inhibitors | |
|---|---|
| 0 Leu | RVKR-NH$_2$ (SEQ ID NO: 1) |
| 1 Leu | LRVKR-NH$_2$ (SEQ ID NO: 2) |
| 2 Leu | LLRVKR-NH$_2$ (SEQ ID NO: 3) |
| 3 Leu | LLLRVKR-NH$_2$ (SEQ ID NO: 4) |
| 4 Leu | LLLLRVKR-NH$_2$ (SEQ ID NO: 5) |
| 5 Leu | LLLLLRVKR-NH$_2$ (SEQ ID NO: 6) |
| 6 Leu | LLLLLLRVKR-NH$_2$ (SEQ ID NO: 7) |
| Multi-Leu (ML) | LLLLRVKR-NH$_2$ (SEQ ID NO: 5) |
| Peptide with optimized stability | |
| Acetyl-ML | CH$_3$CO—NH-LLLLRVKR-NH$_2$ (SEQ ID NO: 5) |
| Peptides with optimized penetration | |
| 8-amino-octanoyl-ML | H$_2$N—CH$_2$—(CH$_2$)$_6$—CO—NH-LLLLRVKR-NH$_2$ (SEQ ID NO: 31) |
| 11-amino-undecanoyl-ML | H$_2$N—CH$_2$—(CH$_2$)$_9$—CO—NH-LLLLRVKR-NH$_2$ (SEQ ID NO: 32) |
| Cholyl-ML | Cholyl-NH-LLLLRVKR-NH$_2$ (SEQ ID NO: 5) |

Enzyme inhibition assays for furin (FIG. 5D) were performed in 100 mM Hepes pH 7.5, 1 mM CaCl$_2$, 1 mM β-mercaptoethanol, 0.5 µg/µL BSA. Assays for PC2 (FIG. 5E) were performed in 20 mM Bis-Tris pH 5,7, 1 mM CaCl$_2$, 0.1% Brij-30. Assays for PC1/3, PC4, PACE4, PC5/6 and PC7 (FIGS. 5F, G, A, B and C respectively) were performed in 20 mM Bis-Tis pH 6.5, 1 mM CaCl$_2$. All assays were performed with the substrate pyroGlu-Arg-Val-Lys-Arg-methyl-coumaryl-7-amide (SEQ ID NO: 33) (PyrRTKR-MCA (SEQ ID NO: 34)) (Bachem, CA) at 100 µM for furin, PC1/3, PC4, PACE4 and PC5/6, 200 µM for PC2 and 250 µM for PC7. Assays were carried out at 37° C. for 30-60 min and real-time fluorescence was measured with an excitation wavelength of 370 nm and an emission wavelength of 460 nM using a Gemini XS™ 96-well spectrofluorometer and Soft-MaxPro4™ software (Molecular Devices, CA). Inhibitory peptides were added to the enzymes at decreasing concentrations from 100 µM to 50 nM and incubated 5 minutes prior to the addition of substrate. Kinetics were analyzed using Soft-MaxPro4™ and K$_i$ values were determined as previously described, using K$_m$ values of 8, 131, 20, 18, 21, 9 and 62 µM for furin, PC2, PC1/3, PC4, PACE4, PC5/6 and PC7, respectively. Each K$_i$ value is the mean of 2 to 10 independent experiments.

As shown in FIG. 5 (peptides are disclosed in Table 2), LRVKR—NH$_2$ (SEQ ID NO: 2) and LLRVKR—NH$_2$ (SEQ ID NO: 3) were mid-nanomolar inhibitors of furin, but the progressive extension by additional leucines decreased the inhibition potency to the micromolar range (FIG. 5D). All multi-leucine peptides were poor micromolar inhibitors of PC2 (FIG. 5E). PC1/3 was best inhibited by LLRVKR—NH$_2$ (SEQ ID NO: 3), but the progressive extension with leucine caused a decrease in potency to the low micromolar range (FIG. 5F). PC4 inhibition potency by multi-leucine peptides generally increased with length (FIG. 5A). The multi-leucine peptide containing five leucines (SEQ ID NO: 6) is the best inhibitor of PC4 evaluated in this study (K$_i$ of 164 nM; FIG. 5G). For PACE4, the progressive extension by multiple leucines caused an increase in inhibition potency to the low nanomolar range (FIG. 5A). LLLLRVKR—NH$_2$ (four leucine or multi-leu peptide; SEQ ID NO: 5) was the most potent inhibitor of PACE4 (K$_i$ of 6 nM) evaluated in this study and was significantly more effective on PACE4 than the other PCs (9-folds and more; FIG. 5A as encircled and in FIG. 6). PC5/6 inhibition increased when adding one or two leucines (SEQ ID NOs: 6 and 7), but the addition of more leucine had a decreasing effect on inhibition potency (FIG. 5B). PC5/6 was best inhibited by LLRVKR—NH$_2$ (SEQ ID NO: 3) in the mid-low nanomolar range. Finally, progressive leucine extensions caused an increase in inhibition potency for PC7 (FIG. 5C). Peptides of four, five and six leucines (SEQ ID NOs: 5, 6 and 7) were similar in potency (K$_i$ values of ~35-50 nM).

Consequently, the multi-leu peptide (SEQ ID NO: 5) represents not only the most potent inhibitor of PACE4, but since the K$_i$ is in the nanomolar range, it also represents a promising inhibitor for in vivo efficacy because of its high selectivity for PACE4.

EXAMPLE 6

Cell Penetration Analysis if PACE4 Inhibitors

Improving the penetration efficacy of identified PACE4 inhibitors was also tested. ML peptide (LLLLRVKR-NH$_2$ (SEQ ID NO: 5), see Table 2) was tested for its ability to enter DU145 cells. Cells were treated with the cholyl-ML peptide linked to FITC. Following FACS scan analysis, control cells are observed in the red spectra. Following treatment, there is a clear shift of the cells indicating that the cholyl-ML FITC peptide has penetrated the cells (FIG. 7A). As a further control, cells were treated with trypsin (FIG. 7B) to insure that the observed shift was not due to the cholyl-ML FITC peptide absorbed on the cell surface. Since, the shifted spectra remains intact, this shows that cholyl-ML FITC peptide has penetrated the cell membranes.

EXAMPLE 7

PACE4 Inhibitors Effects on Cell Proliferation Index

The index of cellular proliferation of cells treated with the ML and acetyl-ML (CH$_3$CO—NH-LLLLRVKR-CONH$_2$ (SEQ ID NO: 5), see Table 2) peptides were measured using the colorimetric MTT assay (thiazolyl blue tetrazolium bromide; Sigma-Aldrich). Briefly, cells were seeded in 96-well plate (BD Biosciences) in triplicate with 100 µl of a 3.5×10$^4$ cells/ml cell suspension in complete growth medium. The following day, cells were carefully washed twice with PBS and media were replaced with 100 µl of either RPMI or conditioned growth media. Conditioned growth medium preparation consists in $1.2 \times 10^5$ cells seeded in 6-well plates with complete growth media. The next day, cells are washed twice with PBS and the media are replaced with 1 ml RPMI growth medium. 48 hours later, the conditioned media are collected, filtered through 0.45 µM syringe filter units and incubated on different cell lines.

48 hours later, 20 µl of a MTT solution (5 mg/ml in PBS 1×) was added to each well for 4.5 h at 37° C./5% $CO_2$. The media was then discarded and the cells were solubilized with 100 µl isopropanol/0.04 N HCl solution. The absorbance was measured at a wavelength of 550 nm with a reference at 650 nm in microplate reader (SpectraMax190™; Molecular Devices).

Four human cell lines were tested, including the small cell carcinoma cell line H345, a gliobastoma cell line U251, the prostatic cell line DU145 and a sarcofibroma cell line HT1080. In all cases, both ML and acetyl-ML peptides had significant effects on the cell proliferation index (FIG. 8 and Table 3). However, acetyl-ML peptides were more potent due to the added protection of the N-terminal acylation.

TABLE 3

| Cell proliferation index | | |
|---|---|---|
| DU145 | ML | acetyl ML |
| Control | 100% | 100% |
| 1 µM | 97.73% | 63.84% |
| 10 µM | 92.03% | 41.91% |
| 50 µM | 72.57% | 25.79% |
| 100 µM | 54.70% | 24.05% |

ML and acetyl-ML peptides with lipid or steroid N-terminal peptides were also compared with the prostatic cell line DU145. As described in FIG. 9, 8-amino-octanoyl-ML ($H_2N$—$CH_2$—$(CH_2)_6$—CO—NH-LLLLRVKR-$NH_2$ (SEQ ID NO: 31) or 11-amino undecanoyl-ML ($H_2N$—$CH_2$—$(CH_2)_9$—CO—NH-LLLLRVKR-$NH_2$ (SEQ ID NO: 32)) or cholyl-ML (cholyl-NH-LLLLRVKR-$NH_2$ (SEQ ID NO: 5)) peptides all had more potent effects than ML or acetyl-ML peptides, most likely due to their additional ability to penetrate the cell membranes (FIG. 9 and Table 4).

TABLE 4

| Cell proliferation index ML and acetyl-ML peptides | | | | | |
|---|---|---|---|---|---|
| DU145 | ML | acetyl ML | 8-amino-octanoyl ML | 11-amino-undecanoyl ML | cholyl ML |
| Control | 100% | 100% | 100% | 100% | 100% |
| 1 µM | 97.73% | 63.84% | 106.05% | 92.44% | 86.65% |
| 10 µM | 92.03% | 41.91% | 97.69% | 35.94% | 38.70% |
| 50 µM | 72.57% | 25.79% | 36.30% | — | — |
| 100 µM | 54.70% | 24.05% | 33.54% | 1.42% | 4.36% |

EXAMPLE 8

PACE4 Inhibitors Effects on the Clonogenic Assay

All ML peptides tested had important effects on the ability of DU145 cell lines to form colonies. Cell lines were seeded in 6-well plates (BD Biosciences) at a density of 300 cells/well in triplicate. DU145 cells were treated for 24 hours with acetyl-ML, 8-amino octanoyl-ML, 11-amino undecanoyl-ML and cholyl-ML at concentrations of 10 and 100 µM. After colony formation, media was discarded and cells were washed once with PBS. Colonies were fixed and stained in 5 mg/ml methylene blue/50% methanol solution for 10 min. Excess of staining solution was removed carefully with distilled water and the plates were dried overnight before scanning with Li-Cor Odyssey Infrared Imaging System™ (Li-Cor Biosciences). Scanned images were analyzed with ImageJ™ software 1.37v to measure the total particle area. The assay was performed in duplicate. As shown on FIGS. 10A and C, the most potent effects were observed with lipid or sterol ML peptides (or octanoyl-ML, white histogram in FIG. 10A).

EXAMPLE 9

PACE4 Inhibitors Effects on In Vivo Formation of Tumor

DU145 cells were implanted subcutaneously (sc) at two sites on the backs of Nu/Nu mice, which lack an immune system. A nude mouse is a genetic mutant that lacks a thymus gland, resulting in an inhibited immune system due to a greatly reduced number of T cells. The genetic basis of the nude mouse mutation is a disruption of the Foxn1 gene. The nude mouse can receive many different types of tissue and tumor grafts, as it mounts no rejection response. These xenografts are commonly used to test new methods of treating tumors. Twenty days after implantation and once tumor had reached an average size of 50 $mm^3$, intra-tumoral cholyl-ML peptide (see Table 2) was injected at a dose of 30 mg/kg, at a frequency of once every 2 days. Control tumor received vehicle (DMSO) injections at the same frequency. Control tumor continued their growth pattern, reaching an average size of 160 $mm^3$, while treated tumors only reached a size of 75 $mm^3$ (FIG. 11A). Representative mice are shown on the B panel of FIG. 11, while the histology of the control and treated tumors are shown in panels C and D of FIG. 11.

EXAMPLE 10

PACE4 Inhibitors Effects on Apoptosis

To determine if the reduced cell number observed in the 4-2 cell line, described previously in Example 3, was a consequence of the induction of the apoptosis, the translocation of phosphatidylserine from the inner to the outer leaflet of the plasma membrane was analyzed. This analysis was performed with a FITC-conjugated annexin-V, which has a strong affinity for these extracellular phosphatidylserines, and the fluorescent intercalating agent propidium iodide (PI). Cell lines were seeded in a 6-well plate at a density of $8 \times 10^4$ cells/well in complete growth medium. The next day, cells were washed twice with PBS and complete growth media with or without cisplatin (Sigma) at final concentration of 66 µM were added. After a 48 hours incubation period, growth media were collected and combined to the harvested cells obtained after trypsin treatment. The collected pellets were washed with PBS before staining. Then, cells were stained with the Annexin-V-FLUOS™ Staining Kit (Roche Applied science), which double labeled cells with annexin-V-fluorescein isothiocyanate (FITC) and propidium iodide (PI). Stained cells were then analyzed with FACScan flow cytometer (BD Biosciences).

FIG. 12 shows the percentage of annexin-V/PI-labeled cells determined by flow cytometry. Both DU145 and 4-2 cell lines exhibited a low level of annexin-V positivity (lower and upper right quadrants; 2% and 3%, respectively) and a similar PI positivity for necrotic cells (upper left quadrant; 6% and 7%, respectively). Treatment with the cytotoxic compound cisplatin induced the apoptosis in both cell lines, since a higher annexin-V positivity was measured for both cell lines (30% and 17% for DU145 and 4-2 cells, respectively). A higher PI staining was also observed, indicating a higher number of dead cells following cisplatin treatment (12% and 16% for DU145 and 4-2 cells, respectively). Thus, these results indicate that apoptosis pathway is still functional, although it is not induced by reduction of PACE4 expression levels.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A paired basic amino acid-cleaving enzyme 4 (PACE4) inhibitor comprising a peptide sequence consisting of the following formula:

$$Y\text{-}Arg_4\text{-}Val_3\text{-}Lys_2\text{-}Arg_1\text{-}NH_2; \quad (\text{SEQ ID NO: 1})$$

wherein $Arg_1$ is an arginine, or an arginine derivative; and

Y comprises the formula $Z\text{-}Xaa_8\text{-}Xaa_7\text{-}Xaa_6\text{-}Xaa_5$, wherein $Xaa_5$, $Xaa_6$, $Xaa_7$ and $Xaa_8$ are Leu, Iso or Val; and Z is absent or comprises an N-terminal acyl group linked to the N-terminal of the peptide sequence.

2. The PACE4 inhibitor of claim 1, wherein $Xaa_5$, $Xaa_6$, $Xaa_7$ and $Xaa_8$ are Leu (SEQ ID NOs:71-73, 79-85, 89-92, 94-97, 103, 106).

3. The PACE4 inhibitor of claim 1, wherein the N terminus is acylated.

4. The PACE4 inhibitor of claim 3, wherein the N terminus acylation is with fatty omega amino acids or with steroid derivatives.

5. The PACE4 inhibitor of claim 4, wherein the steroid derivatives are cholyl.

6. A composition comprising the PACE4 inhibitor as defined in claim 1 and a carrier.

7. The composition of claim 6 further comprising at least one anti-cancer drug.

8. The composition of claim 6 adapted for delivery by at least one of the following routes selected from the group consisting of oral, mucosal, intranasal, intraocular, intratracheal, intrabronchial, intrapleural, intraperitoneal, intracranial, intramuscular, intravenous, intraarterial, intralymphatic, subcutaneous, intratumoral, gastric, enteral, colonic, rectal, urethral and intravesical route.

9. The PACE4 inhibitor of claim 1, wherein said inhibitor is SEQ ID NO: 5.

* * * * *